United States Patent

Kulkarni et al.

Patent Number: 5,994,690
Date of Patent: Nov. 30, 1999

[54] IMAGE ENHANCEMENT IN OPTICAL COHERENCE TOMOGRAPHY USING DECONVOLUTION

[76] Inventors: Manish D. Kulkarni; Joseph A. Izatt; Michael V. Sivak, all of c/o University Hospitals of Cleveland Department of Medicine Division of Gastroenterology 11100 Euclid Ave., Cleveland, Ohio 44106-5066

[21] Appl. No.: 09/040,128
[22] Filed: Mar. 17, 1998

Related U.S. Application Data

[60] Provisional application No. 60/040,798, Mar. 17, 1997.

[51] Int. Cl.⁶ ...................................................... H01J 3/14
[52] U.S. Cl. ................. 250/216; 250/559.4; 250/363.04; 356/347
[58] Field of Search ................................. 250/216, 559.4, 250/559.39, 208.1, 363.02, 363.04; 356/345, 346, 347; 378/4, 36, 37

[56] References Cited

U.S. PATENT DOCUMENTS

| | | | |
|---|---|---|---|
| 4,063,549 | 12/1977 | Beretsky et al. | 128/2 |
| 5,136,172 | 8/1992 | Nakata et al. | 250/559.39 |
| 5,158,090 | 10/1992 | Waldman et al. | 128/664 |
| 5,200,819 | 4/1993 | Nudelman et al. | 358/98 |
| 5,353,802 | 10/1994 | Ollmar | 128/734 |
| 5,459,570 | 10/1995 | Swanson et al. | 356/345 |
| 5,491,524 | 2/1996 | Hellmuth et al. | 351/212 |
| 5,501,226 | 3/1996 | Petersen et al. | 128/691 |
| 5,549,114 | 8/1996 | Petersen et al. | 128/691 |
| 5,565,986 | 10/1996 | Knüttel | 356/346 |

OTHER PUBLICATIONS

*Deconvolution and Enhancement of Optical Coherence Tomograms*, J.M. Schmitt et al., *SPIE*, vol. 2981, pp. 46–57, 64–75 (1997) (Month unknown).

*Phase–Only Blind Deconvolution Using Bicepstrum Iterative Reconstruction Algorithm (BIRA)*, R.S. Holambe et al., *IEEE Transactions on Signal Processing*, vol. 44, No. 9, pp. 2356–2359 (Sep. 1996).

*In Vivo Endoscopic OCT Imaging of Precancer and Cancer Sates of Human Mucosa*, A.M. Sergeev et al., *Optics Express*, vol. 1, No. 13, pp. 432–440 (Dec. 1997).

*Comparison of Some Non–Adaptive Deconvolution Techniques for Resolution Enhancement of Ultrasonic Data*, G. Hayward et al., *Ultrasonics*, vol. 27, pp. 155–164 (May 1989).

*Superresolution Three–Dimensional Images of Fluorescence in Cells with Minimal Ligh Exposure*, W.A. Carrington et al., *Science*, vol. 268, pp. 1483–1487 (Jun. 1995).

(List continued on next page.)

Primary Examiner—Que T. Le
Attorney, Agent, or Firm—Thompson Hine & Flory LLP

[57] ABSTRACT

The present invention provides an improved optical coherence tomography system and involves estimating the impulse response (which is indicative of the actual reflecting and scattering sites within a tissue sample) from the output interferometric signal of an interferometer according to the following steps: (a) acquiring auto-correlation data from the interferometer system; (b) acquiring cross-correlation data from the interferometer system having the biological tissue sample in the sample arm; and (c) processing the auto-correlation data and the cross correlation data to produce an optical impulse response of the tissue. The impulse response may be obtained from the cross-correlation and auto-correlation data by: (d) obtaining an auto-power spectrum from the auto-correlation data by performing a Fourier transform on the auto-correlation data; (e) obtaining a cross-power spectrum from the cross-correlation data by performing a Fourier transform on the cross-correlation data; (f) obtaining a transfer function of the LSI system by taking a ratio of the cross-power spectrum to the auto-power spectrum; and (g) obtaining the optical impulse response of the LSI system by performing an inverse-Fourier transform on the transfer function. Preferably, coherent demodulation is used in combination with the above deconvolution technique to resolve closely-spaced reflecting sites in the sample. By utilizing both the magnitude and phase data of the demodulated interferometric signals, the OCT system of the present invention is able to distinguish between closely spaced reflecting sites within the sample.

39 Claims, 11 Drawing Sheets

OTHER PUBLICATIONS

*Optical Coherence Tomography of Scattering Media Using Frequency Modulated Continuous Wave Techniques with Tunable Near–Infrared Laser*, U. Haberland et al., *SPIE*, vol. 2981 (Proceedings of Coherence Domain Optical Methods in Biomedical Science and Clinical Applications), pp. 20–28 (Feb. 1997).

*Constrained Iterative Restoration Algorithms*, R.W. Schafer et al., *Proceedings of the IEEE*, vol. 69, No. 4, pp. 432–450 (Apr. 1981).

*Blindness Limitations in Optical Coherence Domain Reflectometry*, S.R. Chinn et al., *Electronics Letters*, vol. 29, No. 23, pp. 2025–2027 (Nov. 1993).

*Optical Coherence Tomography*, D. Huang et al. *Science*, vol. 254, pp. 1178–1181 (Nov. 1991).

*Systems and Transforms with Applications in Optics*, A. Papoulis, pp. 254–293 (1968) (Month unknown).

*Maximum–Likelihood Deconvolution, A Journey into Model–Based Signal Processing*, J.M. Mendel, pp. 1–77 (1990) (Month unknown).

*Fundamentals of Statistical Signal Processing: Estimation Theory*, S.M. Kay, pp. 364–371 (1993) (Month unknown).

*Low–coherence Optical Tomography in Turbid Tissue: Theoretical Analysis*, Y. Pan et al., *Applied Optics*, vol. 34, No. 28, pp. 6564–6574 (Oct. 1995).

*Micrometer–Scale Resolution Imaging of the Anterior Eye in Vivo with Optical Coherence Tomography*, J.A. Izatt et al., *Arch Ophthalmol*, vol. 112, pp. 1584–1589 (Dec. 1994).

*Optical Coherence–Domain Reflectometry: A New Optical Evaluation Technique*, R.C. Youngquist et al., *Optics Letters*, vol. 12, No. 3, pp. 158–160 (1987) (Month unknown).

*Spatially Coherent White–light Interferometer Based on a Point Fluorescent Source*, H. Liu et al, *Optics Letters*, vol. 18, No. 9, pp. 678–680 (May 1993).

*High–resolution Reflectometry in Biological Tissues*, X. Clivaz et al., *Optics Letters*, vol. 17, No. 1, pp. 4–6 (Jan. 1992).

*Optical Low Coherence Reflectometry with 1.9μm Spatial Resolution*, X. Clivaz et al., *Electronics Letters*, vol. 28, No. 16, pp. 1553–1555 (Jul. 1992).

*High–speed Optical Coherence Domain Reflectometry*, E.A. Swanson et al., *Optics Letters*, vol. 17, No. 2, pp. 151–153 (Jan. 1992).

*Optical–coherence Tomography of a Dense Tissue: Statistics of Attenuation and Backscattering*, J.M. Schmitt et al., *Phys. Med. Biol.*, 39, pp. 1705–1720 (1994) (Month unknown).

*High–resolution optical coherence tomographic Imaging Using a Mode–locked Ti:Al$_2$O$_3$ Laser Source*, B. Bouma et al., *Optics Letters*, vol. 20, No. 13, pp. 1486–1488 (Jul. 1995).

*Self–phase–modulated Kerr–lens Mode–locked Cr:forsterite Laser Source for Optical Coherence Tomography*, B.E. Bouma et al., *Optics Letters*, vol. 21, No. 22, pp. 1839–1841 (Nov. 1996).

*High–speed Phase– and Group–delay Scanning with a Grating–based Phase Control Delay Line*, G.J. Tearney et al., *Optics Letters*, vol. 22, No. 23, pp. 1811–1813 (Dec. 1997).

*Optical Coherence Tomography Using a Frequency–Tunable Optical Source*, S.R. Chinn et al., *Optics Letters*, vol. 22, No. 5, pp. 340–342 (Mar. 1997).

*Tissue Optics*, D.A. Benaron et al., *Science*, vol. 276, pp. 2002–2003 (Jun. 1997).

*In Vivo Endoscopic Optical Biopsy with Optical Coherence Tomography*, G.J. Tearney, *Science*, No. 276, pp. 2037–2039 (Jun. 1997).

*Fast Algorithms for $1_p$ Deconvolution*, R. Yarlagadda et al., *IEEE Transactions on Acoustics, Speech, and Signal Processing*, vol. ASSP–33, No. 1, pp. 174–182 (Feb. 1985).

*The Design of High–Resolution Digital Filters*, S. Treitel et al., *IEEE Transactions on Geoscience Electronics*, vol. GE–4, No. 1, pp. 25–38 (Jun. 1966).

*A Comprehensive Solution to the Linear Deconvolution Problem*, D.W. Oldenburg, *Geophys. J.R. astr. Soc.*, 65, pp. 331–357 (1981) (Month unknown).

*Digital Processing of Ultrasonic Data by Deconvolution*, E.E. Hundt et al., *IEEE Transactions on Sonics and Ultrasonics*, vol. SU–27, No. 5, pp. 249–252 (Sep. 1980).

*Sternad: Wiener Filter Design Using Polynomial Equations*, A. Ahlén et al., *IEEE Transactions on Signal Processing*, vol. 39, No. 11, pp. 2387–2399 (pp. 2388–2389 missing) (Nov. 1991).

*Maximum Likelihood Estimation of the Attenuated Ultrasound Pulse*, K.B. Rasmussen, *IEEE Transactions on Signal Processing*, vol. 42, No. 1, pp. 220–222 (Jan. 1994).

*Deconvolution of In Vivo Ultrasound Images*, J.A. Jensen, 1990 Ultrasonics Symposium, 1581–1587 (1990) (Month unknown).

*An Iterative Restoration Technique*, S. Singh et al., *Signal Processing*, 11, pp. 1–11 (1986) (Month unknown).

*Video Rate Optical Coherence Tomography*, A.M. Rollins et al., Advances in Optical Imaging & Photon Migration, Trends in Optics & Photonics, Optical Society of America, from the topical meeting Mar. 8–11, 1998, Orlando, Florida (1998).

DEMODULATED DATA

DEMODULATED DATA

MAGNITUDE ONLY DECONVOLUTION

MAGNITUDE ONLY DECONVOLUTION

COMPLEX DECONVOLUTION

COMPLEX DECONVOLUTION

IMAGE ENHANCEMENT IN OPTICAL COHERENCE TOMOGRAPHY USING DECONVOLUTION

CROSS REFERENCE TO RELATED APPLICATIONS

This application claims priority under 35 U.S.C. Sec. 119 from Provisional Patent Application, Ser. No. 60/040,798, filed Mar. 17, 1997; the disclosure of which is incorporated herein by reference.

BACKGROUND

Optical Coherence Tomography (OCT) is a technology that allows for non-invasive, cross-sectional optical imaging in biological media with high spatial resolution and high sensitivity. OCT is an extension of low-coherence or white-light interferometry, in which a low temporal coherence light source is utilized to obtain precise localization of reflections internal to a probed structure along an optic axis. In OCT, this technique is extended to enable scanning of the probe beam in the direction perpendicular to the optic axis, building up a two-dimensional reflectivity data-set, used to create a cross-sectional gray-scale or false-color image of internal tissue backscatter.

OCT has been applied to imaging of biological tissues in vitro and in vivo, although the primary applications of OCT developed to date have been for high resolution imaging of transparent tissues such as the eye. In an OCT image, the detectable intensities of the light reflected from layers of most thick scattering tissues range from $10^{-5}$ to $10^{-10}$th part of the incident power. For most of these studies, compact and inexpensive super luminescent diode sources (SLDs) have been used as interferometer illumination sources. These commercially available SLDs provide ranging resolutions of 15 to 20 $\mu$m (full width at half maximum, i.e., FWHM) in free space. In order to probe ultra-structural details in tissues with fine detail, higher longitudinal resolution is desirable. This is particularly important in the case of non-invasive medical diagnostics, since it is useful to obtain high depth resolution imaging using compact and inexpensive sources which could be easily integrated with endoscopes and catheters.

Epithelial cancers of the breast, lung, and GI tract comprise over 50 percent of all cancers encountered in internal medicine. Many epithelial cancers are preceded by premalignant changes, such as dysplasia or adenoma. Most early GI cancers originate in the superficial layers (i.e., mucosa and submucosa) of the gastrointestinal tract. Because the depth range of OCT imaging is 2 to 3 mm, OCT is sufficient to penetrate superficial tissue layers lining all internal and external free surfaces of the body, including vascular, respiratory, and GI systems, as well as the skin. If axial resolution of OCT images can be optimized to provide cellular resolution (i.e., in the order of 5 $\mu$m), OCT could be used in accurate GI cancer staging and high fidelity diagnosis of precancerous diseases such as Barrette's esophagus and chronic ulcerative colitis.

Because the axial resolution is a function of the coherence length of the low coherence source, typically on the order of 15 $\mu$m, one known attempt to gain high depth resolution has utilized an ultra-short pulse laser as an alternative source of low coherence length illumination. Ranging resolution of 3.7 $\mu$m FWHM has been reported using femtosecond Kerr-lens modelocked TI:Al$_2$O$_3$ laser illumination. A disadvantage with these femtosecond sources is that they are very complicated and expensive, and their medical usage still remains difficult. Accordingly, a need exists for a system that can achieve the high depth resolution imaging utilizing the compact and inexpensive SLDs which can be easily integrated in endoscopes and catheters.

Another problem in known OCT systems, is the formation of unwanted speckle noise in the final gray-scale or false-color image. This speckle noise is caused by the existence of closely spaced reflecting or backscattering sites (located within a coherence length of the SLD to each other) within the sample. Speckle is caused by destructive or constructive interference between the waves backscattered from closely spaced reflecting sites. Because prior art OCT systems have detected only the envelope (i.e., the magnitude data) of the interferometric signal, these systems are unable to resolve the interference between the closely spaced reflectance sites, often producing inaccurate positioning of reflections in addition to spurious reflections in the final image. Accordingly a need also exists for a system that can resolve the closely spaced reflectance sites in the sample, so as to substantially eliminate speckle noise in the final image.

SUMMARY

The present invention involves an advancement in OCT technology which significantly extends the potential applications of OCT. In particular, the present invention substantially increases the resolution of OCT and also increases the information content of OCT images through coherent signal processing of the OCT interferogram data.

To obtain an improved longitudinal resolution in OCT, a transfer function model has been developed for OCT interaction with target tissue, where the impulse response is interpreted as a description of the actual locations of the reflecting and scattering sites within the tissue. Estimation of the impulse response provides the true axial complex reflectivity profile of the is sample with the equivalent of femtosecond resolution.

In this model, the interaction of OCT with tissue is described as a linear shift invariant (LSI) system. The impulse response of the LSI system is interpreted as a description of the actual locations and amplitudes of scattering sites within the sample arising from index of refraction inhomogenities and particulate scatterers in the sample. An interferogram obtained having the sample replaced with a mirror is known as the auto-correlation function of the source optical wave form. The interferogram obtained with the tissue in the sample arm is the measured output of the LSI system, and is known as the cross-correlation function of the incident and backscattered pulse. By obtaining an impulse response profile from the output interferometric signal, using the auto-correlation and cross-correlation functions, a more accurate description of the tissue sample can be obtained.

Accordingly, a method of the present invention involves estimating the impulse response (which is indicative of the actual reflecting and scattering sites within the tissue sample) from the output interferometric signal according to the following steps: (a) acquiring auto-correlation data from the interferometer system with an optical reflector in the sample arm; (b) acquiring cross-correlation data from the interferometer system having the biological tissue sample in the sample arm; and (c) processing the auto-correlation data and the cross correlation data to produce an optical impulse response of the tissue.

The impulse response may be obtained from the cross-correlation and auto-correlation data, in step (c) above, by: (d) obtaining an auto-power spectrum from the autocorrelation data by performing a Fourier transform on the auto-correlation data; (e) obtaining a cross-power spectrum from the cross-correlation data by performing a Fourier transform on the cross-correlation data; (f) obtaining a transfer function of the LSI system by taking the complex conjugate of the ratio of the cross-power spectrum to the auto-power spectrum; and (g) obtaining the optical impulse response of the LSI system by performing an inverse-Fourier transform on the transfer function. For systems that are capable of measuring the cross-power spectra and auto-power spectra directly, steps (f) and (g) may be performed on the measured cross-power and auto-power spectra to generate the optical impulse response.

In a preferred embodiment, coherent demodulation is used in combination with the above deconvolution technique to resolve closely-spaced reflecting sites in the sample. It is advantageous to demodulate the interferometric signals at center wavenumber $k_0$ for achieving quantum noise limited performance. If demodulation is performed outside the computer using an electronic circuit or digital signal processing hardware, complex envelopes of the interferometric signals can be acquired. By utilizing both the magnitude and phase data of the demodulated interferometric signals, the OCT system of the present invention is able to distinguish between closely spaced reflecting sites within the sample. Another advantage of demodulating the interferometric signal is that the demodulated envelopes can be sampled at a lower sampling frequency (than that required for sampling interferograms themselves); and thus, fewer number of samples need to be stored in the computer memory.

The incorporation of demodulation into the deconvolution process is performed according to the following steps: demodulating the auto-correlation and cross-correlation data to acquire the complex envelopes of the auto-correlation and cross-correlation data; obtaining an auto-power spectrum by performing a Fourier transform on the complex envelope of the auto-correlation data; obtaining a cross-power spectrum by performing a Fourier transform on the cross-correlation data; obtaining a transfer function of the system by taking the complex conjugate of the ratio of the cross-power spectrum versus the auto-power spectrum; and obtaining the optical impulse response by performing an inverse-Fourier transform on the transfer function.

In an alternate embodiment, the magnitude data obtained from the above demodulation step may be used, discarding the phase data obtained from the demodulation step. Such an embodiment will obtain enhanced OCT images and will still be able to sample at a lower sample frequency.

Additionally, in the above embodiments, it is advantageous to multiply the transfer function, obtained using the deconvolution technique, with a windowing function (such as a Hanning window) to minimize noise and ringing or sidelobes in the impulse response. It is also advantageous, in the above deconvolution techniques, that the complete auto-correlation and cross-correlation function sequences be measured with sub-micron accuracy. Therefore, to perform this signal acquisition and processing operation, a data acquisition system has been implemented which is capable of compensating for the inevitable velocity fluctuations in the reference mirror speed; and thus, is capable of capturing interferometric data with high accuracy and high signal to noise ratio. This system thus incorporates a long coherence-length calibration interferometer to accurately monitor the reference arm optical path length.

The calibration interferometer preferably uses a narrow-band laser illumination source, such as a Helium-Neon (He—Ne) laser or a Distributed Feedback Diode Laser (DFB Diode Laser), for calibration of the reference arm optical path length. At every reference arm position, both the SLD interferogram and calibration interferogram are measured, and the measured calibration interferogram is used to determine the true position of the reference mirror. Using this information, the true SLD interferogram is interpolated. The corrected low coherence interferometric signal is demodulated and filtered using analog electronics or a digital signal processing algorithm to obtain the complete complex envelope of the interferometric signal (both phase and magnitude).

A method for incorporating the narrow-band illumination source calibration interferometer into the data acquisition system, so as to compensate for the inevitable velocity fluctuations in the reference mirror speed, includes the steps of: extracting a digital clock signal from the measured calibration interferogram data according to a feature of the interferogram data that is regular in time (such as zero crossings), synchronizing the signal acquisition circuitry of the data acquisition system with the extracted digital clock signal (i.e., using the extracted digital clock signal to drive A/D converters to digitize the signal at regular spatial intervals of the reference arm path-length).

An alternate method for incorporating the narrow-band illumination source calibration interferometer into the data acquisition system includes the steps of: digitizing both the calibration and the SLD interferograms at a sampling rate that is higher than twice the frequency of the calibration interferogram; detecting regular features, corresponding to regular intervals of space, of the calibration interferogram (e.g., zero crossings) using a thresholding or pattern recognition algorithm; and re-sample the SLD interferogram data at the regular intervals using interpolation routines.

BRIEF DESCRIPTION OF THE DRAWINGS

FIG. 8a shows magnitude-only deconvolution of the interferogram of FIG. 7a;

FIG. 9a shows complex deconvolution of the interferogram of FIG. 7a; and

DETAILED DESCRIPTION

I. Michelson Interferometer

Figure 1:
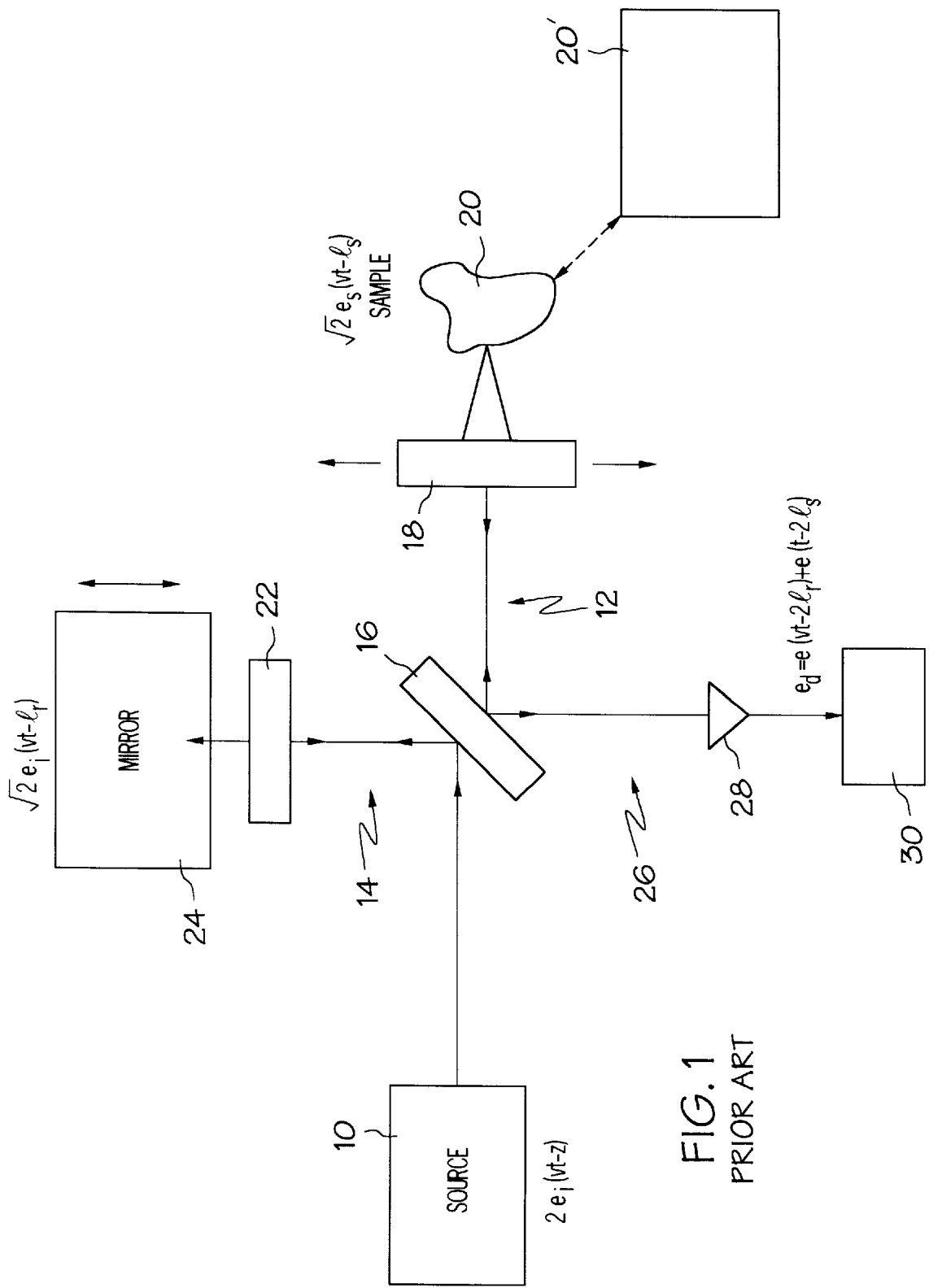
FIG. 1 is a block-diagram representation of a conventional Michelson interferometer.
Figure 2:
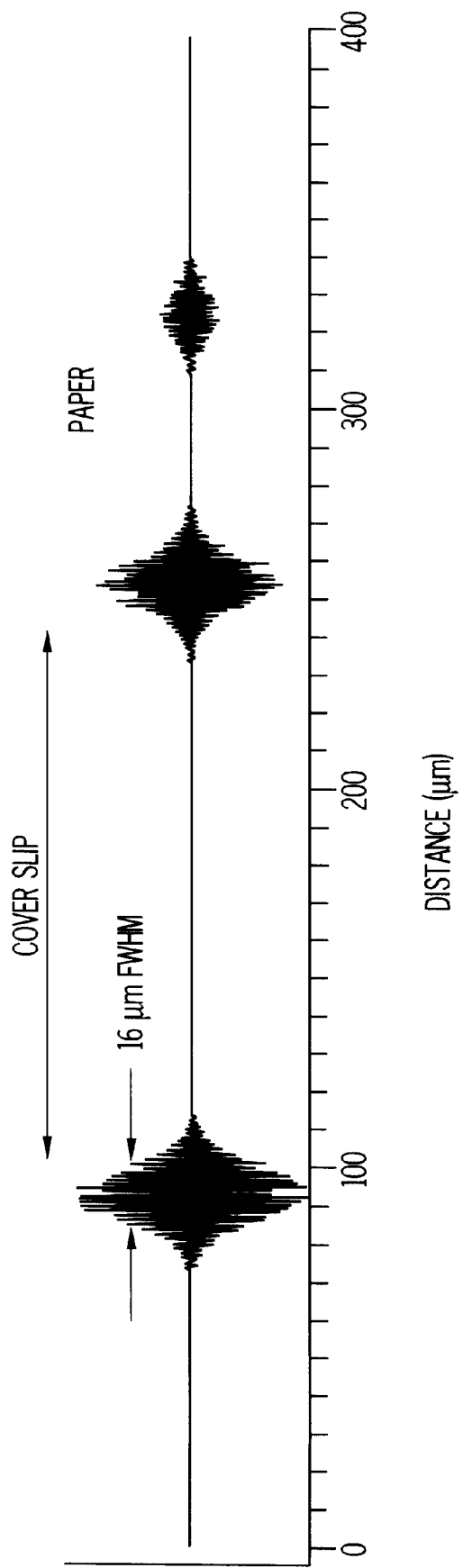
FIG. 2 is an interferogram of a cover slip placed on a piece of paper taken by the Michelson interferometer of FIG. 1.

As shown in FIG. 1, a conventional scanning Michelson interferometer can be utilized to obtain the depth resolved measurements of reflectors and scatterers in a sample. A low coherence light source 10 is separated into two beams by a 50/50 beam splitter 16, fifty percent of the light power is transmitted to a sample arm 12 and the remaining fifty percent is directed to a reference arm 14. The sample arm 12 includes a sample probe 18, which focuses the sample beam into the sample 20 and collects the retroreflected light from the sample. The reference arm 14 includes a reference probe 22 which transmits the reference beam onto a retroreflecting mirror 24, translating towards or away from the reference probe, and collects the light retroreflected back from the mirror 24. The retroreflected beams from the sample 20 and mirror 24 are combined again in the beam splitter 16 into a detected electric field 26, which is directed to the optical detector 28. Because a low coherence light source 10 is used, an interferometric signal is produced at the detector 28 when the sample probe path distance to a reflecting or scattering site within the sample 20 matches the reference arm length, to within a source coherence length. For every reflecting or scattering site within the sample, a fringe pattern will appear in the interferometric signal similar to that as shown in FIG. 2. The axial profiles of backscatter versus depth are measured by translating the reference mirror 24 and by synchronously recording the envelope of the interferometric signal at the detector 28. This profile is known as the OCT A-scan of the sample. Two dimensional cross-sectional imaging of the sample is performed by laterally scanning the sample probe 18 during successive A-scans. The resulting data set is processed in a computer 30 and displayed as a gray scale or false color image. A series of two-dimensional images can be acquired by scanning the probe beam perpendicular to the direction of lateral scanning. The series of two-dimensional images can then be rendered into a three dimensional display or a pseudo three dimensional display in gray scale or false color.

Those of ordinary skill in the art will recognize that, although it is preferred to scan the sample probe 18 with respect to the sample 20, the sample may also be scanned with respect to a stationary sample probe. It will also be recognized that the technique of optical coherence domain reflectometry (OCDR) is very similar in nature to OCT. OCDR measures profile of reflectivity as a function of depth in a specimen, and essentially measures OCT A-scans. Accordingly, the inventions described herein are also applicable to OCDR systems and for the purposes of this disclosure the terms OCT and OCDR will be used interchangeably. It also to be understood, that for the purposes of this disclosure, the term "optical" is to pertain to all ranges of electromagnetic radiation, and preferably pertains to the range of 100 nanometers to 30,000 nanometers.

In developing the present invention, a unique transfer function model has been developed for OCT interaction with the sample, where the impulse response is interpreted as a description of the actual locations of the reflecting and scattering sites within the sample. Based upon this model, The transfer function of the system can be calculated from the source auto-power spectrum and the cross-power spectrum of the electric fields in the reference and sample arms. The estimation of the impulse response from the transfer function provides the true axial complex reflectivity profile of the sample with the equivalent of femtosecond temporal resolution.

II. Transfer Function Model

In this transfer function model, the interaction of OCT with the sample is described as a linear shift invariant (LSI) system. The optical impulse response h(z), where z indicates depth within a specimen, provides deconvolved information regarding actual locations and amplitudes of reflecting and scattering sites within the sample arising from index of refraction inhomogenities and particulate scatters in the sample. The impulse response h(z) is taken from the inverse Fourier transform of the transfer function H(k) (k indicates wavenumber) of the LSI system.

The derivation of the transfer function model is as follows: A source electric field, expressed in scalar form as 2 (vt−z), is assumed to be incident on the interferometer. We assume that the center wavenumber of the source field or the source power spectrum is $k_0$. Here z is the space variable in both arms, t indicates time and v is the group velocity at the source center frequency. Group velocity dispersion in the sample is assumed to be negligible over a typical scan depth of a few millimeters. $l_r$ and $l_s$ are the optical path lengths in the reference and sample arms, respectively. Assuming an ideal reference mirror, $\sqrt{2}\tilde{e}_r(vt-2l_r)$ and $\sqrt{2}\tilde{e}_s(vt-2l_s)$ are the fields returning from the reference and sample arms, respectively. Note that $\tilde{e}_r(vt-z)=e_r(vt-z)\exp(-j2\pi k_0(ct-z))$ and $\tilde{e}_s(vt-z)=e_s(vt-z)\exp(-j2\pi k_0(ct-z)))$ where c indicates the phase velocity of the wave and $j=\sqrt{-1}$. Here $e_i$ and $e_s$ represent the complex envelopes of the electric fields, $\tilde{e}_r(vt-z)$ and $\tilde{e}_s(vt-z)$, respectively. The detector current is proportional to the temporal average of the detected field power $|\tilde{e}_d|^2$. Mechanically scanning the reference arm length generates an alternating component of the detector current which is a cross-correlation of $\tilde{e}_i$ and $\tilde{e}_s$ and is a function of the round-trip optical path length difference between the reference and sample arms $\Delta l=2(l_r-l_s)$.

An interferogram obtained having the sample 20 replaced with a mirror 20' in the sample arm 12, is the "auto-correlation function" $\tilde{R}_{ii}(\Delta l)$ of the source optical wave form and is treated as an input to the LSI system. The interferogram obtained with the sample 20 in the sample arm 12 is the measured output of the LSI system, known as the "cross-correlation function" $\tilde{R}_{is}(\Delta l)$. The correlation functions are expressed as $$\tilde{R}_{is}(\Delta l)=<\tilde{e}_i(vt)\tilde{e}_s^*(vt+\Delta l)>, \tilde{R}_{ii}(\Delta l)=<\tilde{e}_i(vt)\tilde{e}_i^*(vt+\Delta l)> \quad (1)$$

where <> denotes averaging over the response time of the detector. According to the Wiener-Khinchin theorem, the Fourier transforms of the auto-correlation and cross-correlation functions are the auto-power and cross-power spectra denoted by $\tilde{S}_{ii}(k)$ and $\tilde{S}_{is}(k)$, respectively, where k represents wavenumber.

As discussed above, the impulse response h(z) is interpreted as a description of the actual locations and amplitudes of reflecting and scattering sites within the sample arising from refractive index inhomogeneities and particulate scatterers. The backscattered electric field is given by $$\tilde{e}_s(z) = \tilde{e}_i(z) \otimes h(z) \qquad (2)$$

where $\otimes$ represents convolution. Note that shift invariance allows omission of the terms vt in this expression. The convolution theorem leads to $$\tilde{E}_s(k) = \tilde{E}_i(k)H(k) \qquad (3)$$

where $\tilde{E}_s(k)$, $\tilde{E}_i(k)$, and H(k) are the Fourier transforms of $\tilde{e}_s(z)$, $\tilde{e}_i(z)$, and h(z), respectively. H(k) is the system transfer function. Inserting Eq. 2 in Eq. 1 leads to $$\tilde{R}_{is}(\Delta l) = \tilde{R}_{ii}(\Delta l) \otimes h^*(-\Delta l), \tilde{S}_{is}(k) = \tilde{S}_{ii}(k)H^*(k) \qquad (4)$$

$$\Rightarrow H^*(k) = \tilde{S}_{is}(k)/\tilde{S}_{ii}(k) \qquad (5)$$

The superscript * indicates a complex conjugate. Simply put, the auto-power and cross-power spectra, $\tilde{S}_{ii}(k)$ and $\tilde{S}_{is}(k)$, are the Fourier transforms of the cross-correlation and auto-correlation functions, $\tilde{R}_{ii}(\Delta l)$ and $\tilde{R}_{is}(\Delta l)$, respectively; and the complex conjugate of the transfer function H*(k) is the ratio of the cross-power spectra and the auto-power spectra.

In practice, the correlation functions defined in Eq. 1 are hard to measure. The measured (or estimated) correlation functions are influenced by the properties of the optical elements, the measurement electronics, and data acquisition systems, and various noise sources. Therefore what we measure are "estimates" of $\tilde{R}_{ii}(\Delta l)$ and $\tilde{R}_{is}(\Delta l)$. However, for the description of deconvolution algorithms and claims we will still use the symbols $\tilde{R}_{ii}(\Delta l)$ and $\tilde{R}_{is}(\Delta l)$ to indicate the "estimates" of auto-correlation and cross-correlation functions, respectively. For the purposes of clarity, the terms "auto-correlation and cross-correlation functions" may be used for the terms, "the estimates of auto-correlation and cross-correlation functions" in describing the present inventions.

Similarly the measured (or estimated) power spectra are influenced by the properties of the optical elements, the measurement electronics, and data acquisition systems, and various noise sources. Therefore what we measure are "estimates" of $\tilde{S}_{ii}(k)$ and $\tilde{S}_{is}(k)$, However, for the description of deconvolution algorithms and claims we will still use the symbols $\tilde{S}_{ii}(k)$ and $\tilde{S}_{is}(k)$, to indicate the "estimates" of auto-power and cross-power spectra, respectively. For the purposes of clarity, the terms "auto-power and cross-power spectra" may be used for the terms, "the estimates of auto-power and cross-power spectra" in describing the present inventions.

In the setups where the group velocity is different than the phase velocity, the method is applicable if v is interpreted as group velocity. Also, while we describe the specific case of a device which uses infra-red light source, the deconvolution procedure is applicable to any interferometric device illuminated by any electromagnetic radiation source.

In Eq. 2, we describe the light-specimen interaction as a linear shift invariant system. We describe the deconvolution methods based on Eq. 5. It should be apparent to a person skilled in the art that the interaction described by Eq. 2 and/or Eq. 4 can be exploited by many other methods in space/time domain including iterative deconvolution methods, CLEAN deconvolution algorithm, etc. This model also forms the basis of "blind" deconvolution methods which do not use a priori information about the auto-correlation function but assume that it convolves with the impulse response.

The true transfer function H(k) is rarely estimated or measured. In most practical cases, what we get is an "estimate" of the transfer function which is different than the true transfer function. One can obtain this estimate in various ways. One such method is taking the ratio of cross-power spectrum and the auto-power spectrum and omitting the step of complex conjugation.

Mechanical elements rarely perform a perfect job in scanning the optical path lengths or measuring optical spectra. Since the spectra and correlation functions play a major role in deconvolution, it is useful to have the means to correct for irregularities in the scan rate of the optical path length difference between the reference path and the sample path or the irregularities in measuring the spectra. As will be described below, we have developed a calibration interferometer to achieve such corrections.

III. Deconvolution of Interferograms

Figure 3A:
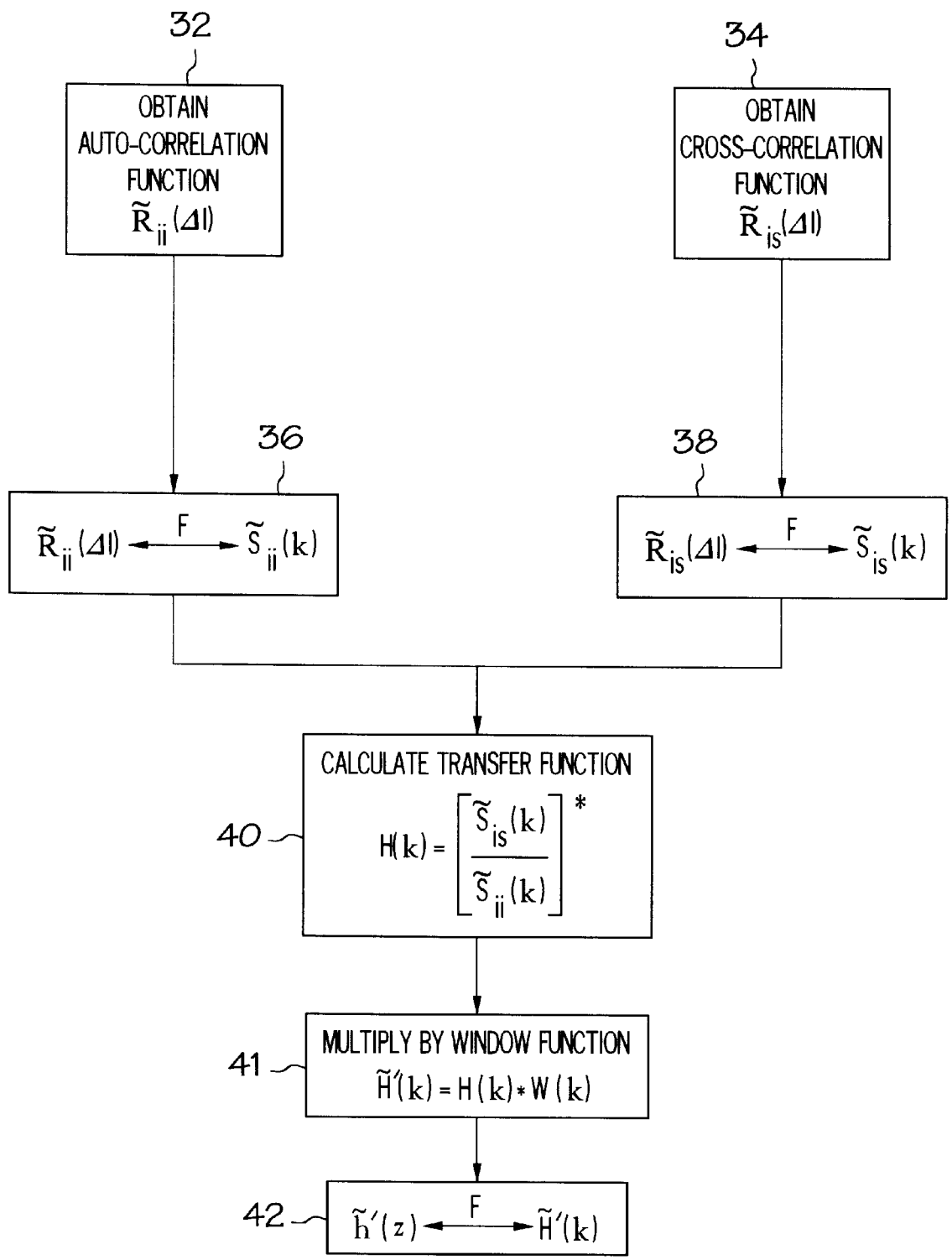
FIG. 3a is a flow-diagram representation of a first embodiment of an OCT image enhancement method of the present invention.

Accordingly, based upon the above transfer function model, the present invention provides an access to understanding of interaction of the specimen with the electric fields themselves by performing simple correlation measurements using a Michelson interferometer. The impulse response is estimated from the output interferometric signal according to the steps as illustrated in FIG. 3a. As indicated in step 32, the auto-correlation function $\tilde{R}_{ii}(\Delta l)$ is acquired from an OCT system having an optical reflector in the sample arm; and as indicated in step 34, the cross-correlation function $\tilde{R}_{is}(\Delta l)$ is acquired from the OCT system having the biological tissue sample in the sample arm. As indicated in step 36, the auto-power spectrum $\tilde{S}_{ii}(k)$ is obtained from the auto-correlation data by performing a Fourier transform on the auto-correlation data $\tilde{R}_{ii}(\Delta l)$; and as indicated in step 38, the cross-power spectrum $\tilde{S}_{is}(k)$ is obtained from the cross-correlation data by performing a Fourier transform on the cross-correlation data $\tilde{R}_{is}(\Delta l)$. As indicated in step 40, the transfer function H(k) of the system is given by the complex conjugate of the ratio of the cross-power spectrum $\tilde{S}_{is}(k)$ versus the auto-power spectrum $\tilde{S}_{ii}(k)$. Since the source spectrum has a finite bandwidth, in order to minimize noise in the impulse response, as indicated in step 41, the estimate of the transfer function is multiplied by a Fourier (i.e., frequency) domain windowing function W(k) to minimize noise and ringing or sidelobes in the impulse response. We denote transfer function estimated in this manner by $\tilde{H}'(k)$. As indicated in step 42, the estimated impulse response $\tilde{h}'(z)$ is obtained by performing an inverse-Fourier transform on the estimated transfer function $\tilde{H}'(k)$.

As will be discussed below, the estimated impulse response data $\tilde{h}'(z)$ can be transmitted to a computer for further processing. The computer may create a two-dimensional cross-sectional deconvolved gray-scale or false-color image of the sample by laterally scanning the sample probe between the acquisition of successive A-scans to obtain a plurality of impulse responses $\tilde{h}'(z)$, one for each lateral point of the sample. A one-dimensional axial reflectivity profile can be obtained for each impulse response $\tilde{h}'(z)$ by demodulating the impulse response $\tilde{h}'(z)$ and by plotting the magnitude data therefrom. The magnitudes of the complex envelopes of deconvolved impulse responses $\tilde{h}'(z)$ could also be estimated by an incoherent envelope detection technique. Finally, the two-dimensional image is obtained by aligning the one-dimensional interferograms side-by-side in sequence.

Figure 4A:
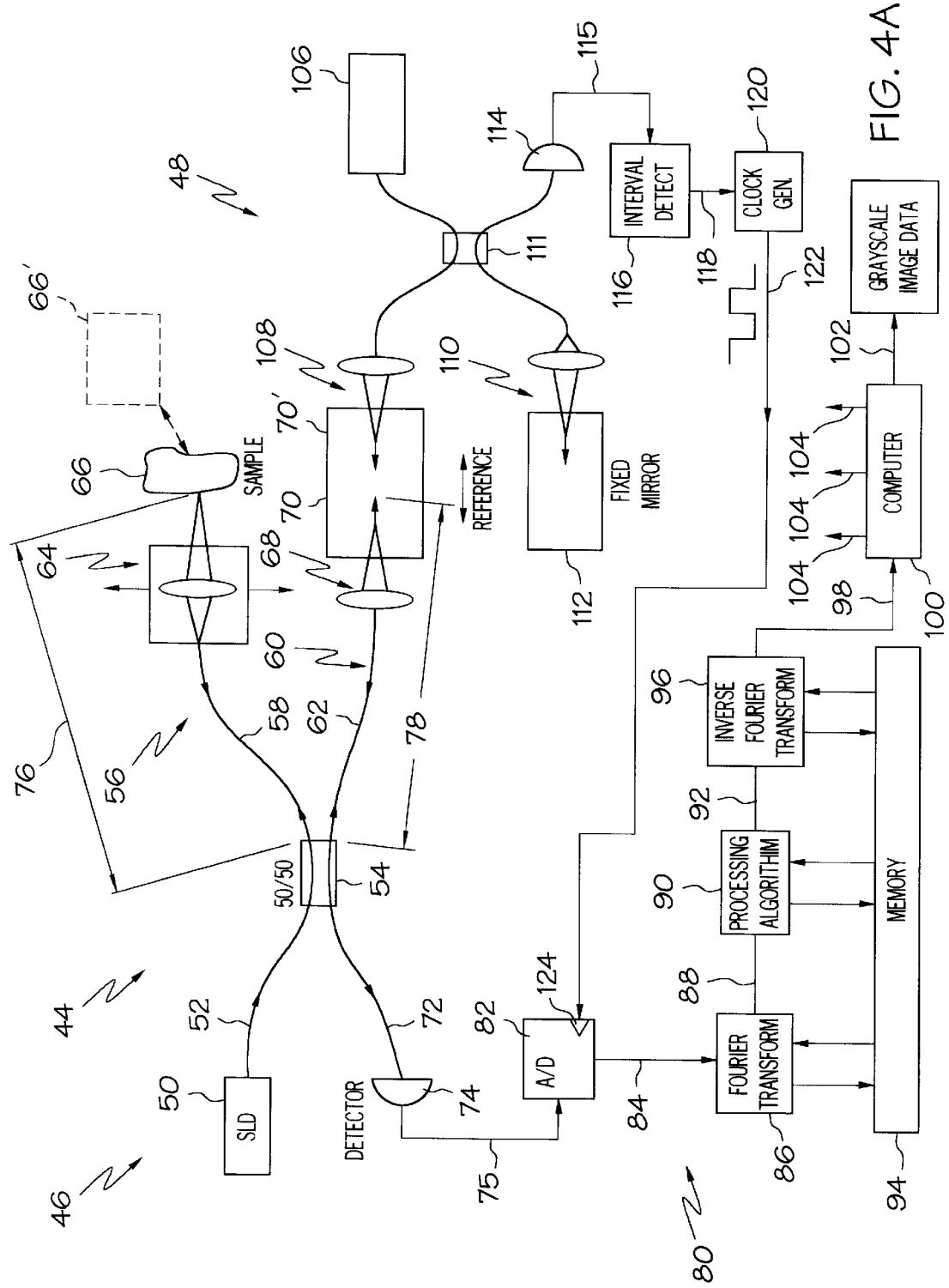
FIG. 4a is a block-diagram representation of an OCT data-acquisition system for performing the first embodiment of the OCT enhancement method of the present invention.

As shown in FIG. 4a, an OCT data acquisition system 44 for performing the above method includes a low-coherence interferometer 46 and, preferably, a calibration interferometer 48. The low-coherence interferometer includes a light source, such as a super-luminescent diode ("SLD") source 50, a fiber-optic source line 52 coupled between the SLD 50 and a fiber-optic beam splitter (such as a 50/50 fiber coupler) 54. The beam splitter separates the light received from the source line 52 into two beams; one transmitted to a sample arm 56 via an optical fiber 58, and the other to a reference arm 60 via an optical fiber 62. The fiber 58 is coupled to a sample probe 64 adapted to focus light to a sample 66 and to receive the light reflected back from the sample 66. The reflected light received back from the sample is transmitted back to the beam splitter 54 via the fiber 58. Preferably, the sample probe 64 has an adjustable focal length, thus allowing the adjustment of the focal spot size.

The fiber 62 is coupled to a reference probe 68 adapted to focus the light received from the fiber 62 to a translating reference mirror 70 (usually mounted on a galvanometer), and to receive the light reflected back from the reference mirror 70. The reflected light received back from the reference mirror is transmitted back to the beam splitter 54 via the fiber 62. The reflected light received by the beam splitter 54, back from both the fiber 58 and fiber 62, is combined and transmitted on the fiber-optic line 72 to the photodetector 74. The photodetector 74 produces an analog signal 75 responsive to the intensity of the incident electric field. An example of a photodetector for use with the present invention is a Model 2011, commercially available from New Focus, Inc., Mountain View, Calif.

The optical path length 76 of the sample arm 56 remains constant, while the optical path length 78 of the reference arm 60 changes with the translation of the reference mirror 70. Because a low coherence light source is used, a fringe pattern (interferometric signal) is produced at the photodetector 74 the optical path length 76 to a reflecting or scattering site within the sample 66 matches the optical path length 78 of the reference arm 60 within a coherence length. Recording the detector current while translating the reference mirror 70 provides interferogram data, which is the optical path length dependent cross-correlation function $\tilde{R}_{is}(\Delta l)$ of the light retroreflected from the reference mirror 70 and the sample 66. Collecting interferogram data for a point on the surface of the sample for one reference mirror cycle is referred to as collecting an "A-scan." The A-scan data provides a one-dimensional profile of reflecting and scattering sites of the sample 66 verses depth.

The analog interferogram data signal 75 produced by the photodetector 74, for each A-scan, is sent through deconvolution scheme 80, designed to perform the steps as described above in FIG. 3a. The deconvolution scheme 80 includes an analog-to-digital converter 82 for converting the analog interferogram data 75 produced by the photodetector 74 into a digital interferogram signal 84. The digital interferogram signal 84 is sent to a Fourier transform algorithm 86 for obtaining the cross-power spectrum $\tilde{S}_{is}(k)$ data 88. Fourier transform algorithm for use with the present invention is available in software libraries in commercially available software packages such as LabVIEW supplied by National Instruments, Austin, Tex.

The cross-power spectrum data is then sent to a processing algorithm 90 for calculating the transfer function estimate $\tilde{H}'(k)$ data 92. The processing algorithm 90 is coupled to a memory 94 for storing the auto-power spectrum data. To obtain the auto-power spectrum data, at some point either before or after measurement of the sample, the sample 66 is replaced by a mirror 66' and the data received by the photodetector 74 is the optical path length dependent auto-correlation function $\tilde{R}_{ii}(\Delta l)$ of the source light generated from the light retroreflected from the reference mirror 70 and the sample mirror 66'. The analog-to-digital converter 82 converts the analog auto-correlation function 75 into a digital signal and the Fourier transform algorithm 86 then obtains the auto-power spectrum $\tilde{S}_{ii}(k)$ data 88. When the processing algorithm 90 receives the auto-power spectrum $\tilde{S}_{ii}(k)$ data, it stores the data in the memory 94. Accordingly, the processing algorithm 90 will have access to the auto-power spectrum $\tilde{S}_{ii}(k)$ for calculating the estimate of the transfer function H(k) as described above.

The estimate of the transfer function H(k) 92 of the system is preferably obtained by the processing algorithm 90 according to a complex conjugate of the ratio of the cross-power spectrum $\tilde{S}_{is}(k)$ versus the auto-power spectrum $\tilde{S}_{ii}(k)$. Since the source spectrum has a finite bandwidth, in order to minimize noise in the impulse response, the estimate of the transfer function is multiplied by a windowing function to minimize noise and ringing or sidelobes in the impulse response. Generally, the windowing function is centered at the wavenumber of the SLD illumination source 50; and is a bell-shaped function narrow enough to eliminate the noise and wide enough to achieve the desired resolution. An example of such a windowing function is a Hanning window. The windowing can also be performed by multiplying the window function W(k) and the cross-power spectrum $\tilde{S}_{is}(k)$ and then dividing the product by the auto-power spectrum $\tilde{S}_{ii}(k)$. Alternatively, one can divide W(k) by $\tilde{S}_{ii}(k)$ and then multiply the ratio by $\tilde{S}_{is}(k)$. Another way of achieving the same result is, dividing the auto-power spectrum $\tilde{S}_{ii}(k)$ by W(k) and then using the result to divide the cross-power spectrum $\tilde{S}_{is}(k)$.

Figure 5:
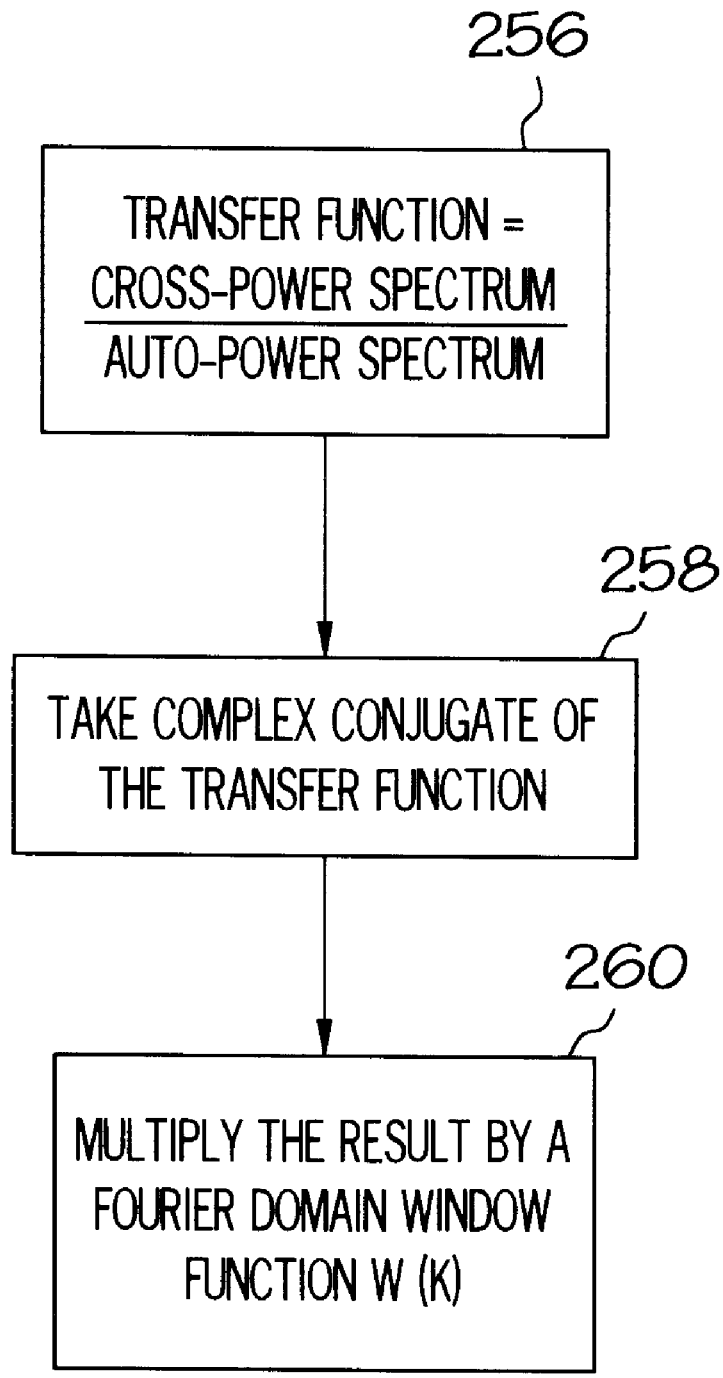
FIG. 5 is a flow-diagram representation of processing steps performed by a processing algorithm for use with the present invention.

The detailed steps performed by the processing algorithm 90 are shown in FIG. 5. First, as indicated in step 256, the cross-power spectrum is divided by the auto-power spectrum; and, as indicated in step 258, the result is complex conjugated. Then, as indicated in step 260, the resulting function is multiplied by a Fourier domain windowing function. We denote transfer function estimated in this manner by $\tilde{H}'(k)$.

Referring again to FIG. 4a, once the transfer function estimate $\tilde{H}'(k)$ 92 is calculated, the transfer function estimate $\tilde{H}'(k)$ data is transmitted to an inverse-Fourier transform algorithm 96 for obtaining the impulse response estimate $\tilde{h}'(z)$ data 98 from the transfer function estimate $\tilde{H}'(k)$ data. An inverse Fourier transform algorithm 96 for use with the present invention is available in commercially available software packages such as LabVIEW supplied by National Instruments, Austin, Tex.

Note that the operations described herein have been performed and tested in software using packages such as LabVIEW and MATLAB. It is also within the scope of the invention that these operations be performed by using hardware DSP devices and circuitry. For example, the Fourier transform algorithm 86, the processing algorithm 90 and the inverse-Fourier transform algorithm 96 may be performed by hardware devices or circuits specially designed to perform the steps as described above. Such hardware devices or circuits are conventional and thus will be apparent to those of ordinary skill in the art.

The impulse response estimate $\tilde{h}'(z)$ data 98 is transmitted to a computer 100 for creation of the two-dimensional (2-D) deconvolved gray-scale or false-color image data 102. Generally, this includes the steps of: passing the impulse response $\tilde{h}'(z)$ is through an envelope detector to obtain its envelope, and aligning the envelopes of adjacent impulse response estimates $\tilde{h}'(z)$ to generate a 2-D image. The envelope detection can be performed by various means. One such method is use a coherent demodulator and perform demodulation at wavenumber (i.e., spatial frequency $k_0$) to obtain the complex envelope of $\tilde{h}'(z)$ and retaining the magnitude of the complex envelope. Intensity of the 2-D image can be encoded by various means including gray-scale and false-color rendering.

The computer 100 also preferably generates the control signals 104 for controlling the above process. For example, the computer may simultaneously control the lateral translation of the sample probe 64 and the translation of the reference mirror 70; and the computer 100 may also provide controls for coordinating the deconvolution scheme 80. Furthermore, it should be apparent to one of ordinary skill in the art, that the computer 100, could contain all or portions of the deconvolution scheme 80, or that the deconvolution scheme could be part of a separate analog or digital circuit, etc.

IV. Demodulated Magnitude-only Deconvolution

The complex envelope of an interferogram obtained having the sample 20 replaced with a mirror 20' in the sample arm 12, is the auto-correlation function $R_{ii}(\Delta l)$ of the complex envelopes of the electric fields. The complex envelope of an interferogram obtained with the sample 20 in the sample arm 12 is the measured output of the LSI system, and is also the cross-correlation function $R_{is}(\Delta l)$ of the complex envelopes of the electric fields. Note that $R_{ii}(\Delta l)$ and $R_{is}(\Delta l)$ are complex envelopes of $\tilde{R}_{ii}(\Delta l)$ and $\tilde{R}_{is}(\Delta l)$, respectively (i.e., $\tilde{R}_{is}(\Delta l) = R_{is}(\Delta l) \exp(-j2\pi k_0 \Delta l)$, $\tilde{R}_{ii}(\Delta l) = R_{ii}(\Delta l) \exp(-j2\pi k_0 \Delta l)$). The correlation functions are expressed as:

$$R_{is}(\Delta l) = \langle e_i(vt) e_s^*(vt+\Delta l) \rangle$$

$$R_{ii}(\Delta l) = \langle e_i(vt) e_i^*(vt+\Delta l) \rangle \tag{6}$$

where $e_i$ and $e_s$ represent the complex envelopes of the electric fields, (i.e., $\tilde{e}_i(vt-z) = e_i \exp(-j2\pi k_0(ct-z))$ and $\tilde{e}_s(vt-z) = e_s \exp(-j2\pi k_0(ct-z))$) where c indicates the phase velocity of the wave and $j=\sqrt{-1}$. According to the Wiener-Khinchin theorem, the Fourier transforms of the auto-correlation and cross-correlation functions are the auto-power and cross-power spectra denoted by $S_{ii}(k)$ and $S_{is}(k)$, respectively, where k represents wavenumber. Note that current OCT systems acquire only magnitudes of complex envelopes, i.e., $|R_{is}(\Delta l)|$ and $|R_{ii}(\Delta l)|$. According to our model, the complex envelope of the backscattered electric field is given by $$e_S(z) = e_i(z) \otimes h(z) \tag{7}$$

The convolution theorem leads to $$E_s(k) = E_i(k) H(k) \tag{8}$$

where $E_s(k)$ and $E_i(k)$ are the Fourier transforms of $e_s(z)$ and $e_i(z)$, respectively. Inserting Eq. 7 in Eq. 6 leads to $$R_{is}(\Delta l) = R_{ii}(\Delta l) \otimes h^*(-\Delta l), \tag{9}$$

$$S_{is}(k) = S_{ii}(k) H^*(k)$$

$$H^*(k) = S_{is}(k)/S_{ii}(k) \tag{10}$$

Simply put, the auto-power and cross-power spectra, $S_{ii}(k)$ and $S_{is}(k)$, are the Fourier transforms of the cross-correlation and auto-correlation functions, $R_{ii}(\Delta l)$ and $R_{is}(\Delta l)$, respectively; and the complex conjugate of the estimate of the transfer function $H^*(k)$ is the ratio of the cross-power spectra and the auto-power spectra.

If only magnitudes of the correlation functions are acquired, then estimates of the power spectra are obtained by taking the Fourier transforms of $|R_{is}(\Delta l)|$ and $|R_{ii}(\Delta l)|$ denoted by $S_{is}'''(k)$ and $S_{ii}'''(k)$, respectively. The transfer function estimated this way is denoted by $H'''(k)$ and is given by $H'''(k) = (S_{is}'''(k)/S_{ii}'''(k))^*$. Inverse Fourier transforming $H'''(k)$ would give an estimate of the impulse response $h'''(z)$ which is essentially a sharpened OCT A-scan. We define sharpness improvement as the decrease in the widths of isolated reflections in the A-scans.

Figure 3B:
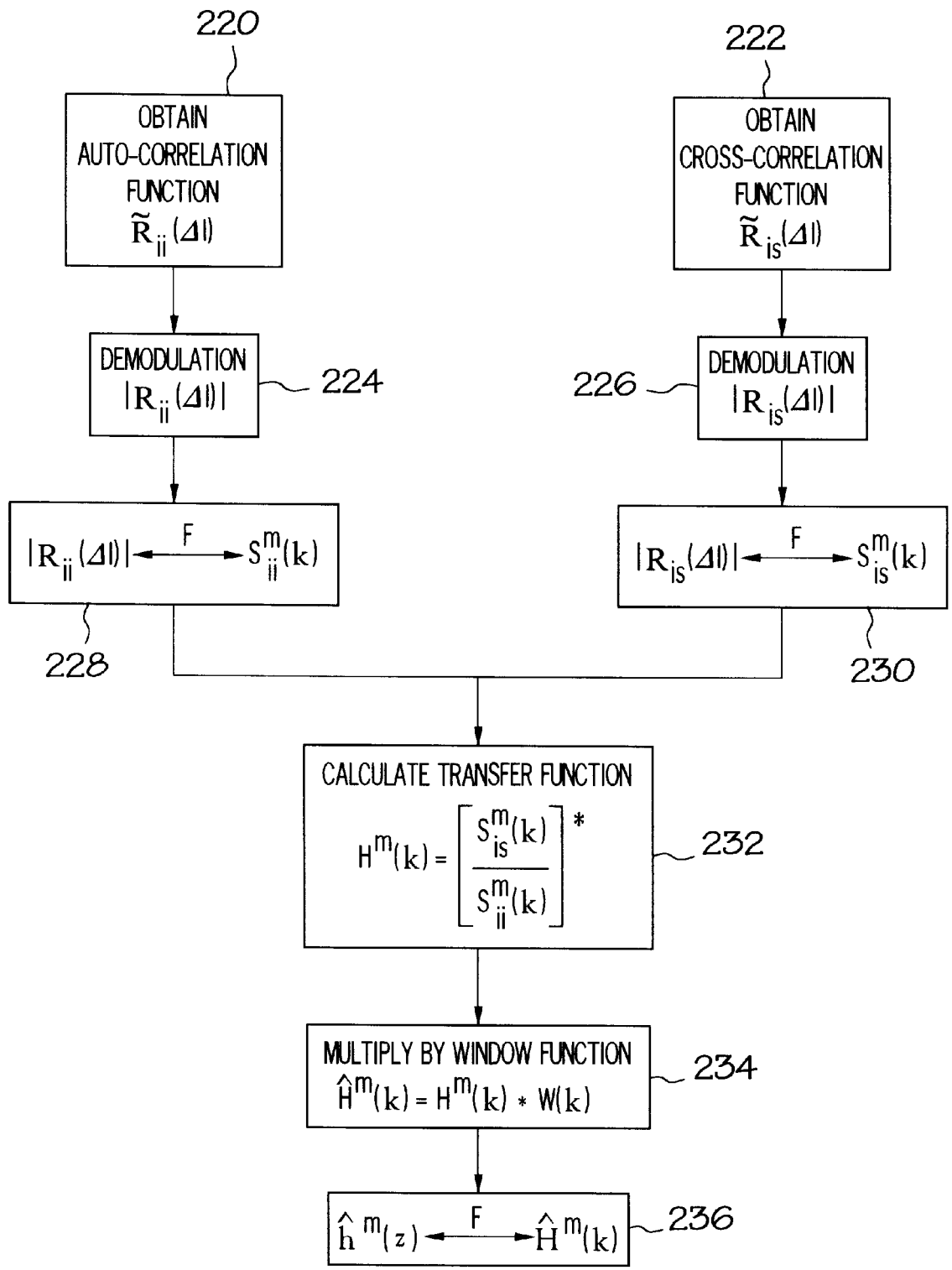
FIG. 3b is a flow-diagram representation of a second embodiment of an OCT image enhancement method of the present invention.

Accordingly, the impulse response is estimated from the cross-correlation function according to the steps as illustrated in FIG. 3b. As indicated in step 220, the auto-correlation function $\tilde{R}_{ii}(\Delta l)$ of electric fields is acquired from an OCT system having an optical reflector in the sample arm; and, as indicated in step 222, the cross-correlation function $\tilde{R}_{is}(\Delta l)$ is acquired from the OCT system having the biological tissue sample in the sample arm. In steps 224 and 226, the magnitudes of complex envelopes, viz., $|R_{ii}(\Delta l)|$ and $|R_{is}(\Delta l)|$ are acquired by demodulating the interferometric signals. This envelope detection can be performed by various means. One such method is use a coherent demodulator and perform demodulation at wavenumber (i.e., spatial frequency) $k_0$ to obtain the complex envelope of $\tilde{R}_{is}(\Delta l)$ (or $\tilde{R}_{ii}(\Delta l)$) and retaining the magnitude of the complex envelope.

As indicated in step 228, the auto-power spectrum estimate $S_{ii}{}^m(k)$ is obtained by performing a Fourier transform on $|R_{ii}(\Delta l)|$; and, as indicated in step 230, the cross-power spectrum estimate $S_{is}{}^m(k)$ is obtained by performing a Fourier transform on the cross-correlation function $|R_{is}(\Delta l)|$. As indicated in step 232, the transfer function estimate $H^m(k)$ of the system is estimated by taking complex conjugates of the ratio of the cross-power spectrum estimate $S_{is}{}^m(k)$ versus the auto-power spectrum estimate $S_{ii}{}^m(k)$. Since the source spectrum has a finite bandwidth, in order to minimize noise in the impulse response, as indicated in step 234, the estimate of the transfer function is multiplied by a windowing function to minimize noise and ringing or sidelobes in the impulse response. The windowing can also be performed by multiplying the window function W(k) and the cross-power spectrum $S_{is}{}^m(k)$ and then dividing the product by the auto-power spectrum $S_{ii}{}^m(k)$. Alternatively, one can divide W(k) by $S_{ii}{}^m(k)$ and then multiply the ratio by $S_{is}{}^m(k)$. Another way of achieving the same result is, dividing the auto-power spectrum $S_{ii}{}^m(k)$ by W(k) and then using the result to divide the cross-power spectrum $S_{is}{}^m(k)$.

As indicated in step 236, the transfer function estimated in this manner is given by $\hat{H}^m(k)$. The estimated impulse response $\hat{h}^m(z)$ is obtained by performing an inverse-Fourier transform on the estimated transfer function $\hat{H}^m(k)$.

As discussed above, the estimated impulse response data $\hat{h}^m(z)$ can be transmitted to the computer 100 for further processing, such as developing the two-dimensional cross-sectional deconvolved gray-scale or false-color image of the sample. The magnitude of $\hat{h}^m(z)$ is used for displaying the image.

Figure 4B:
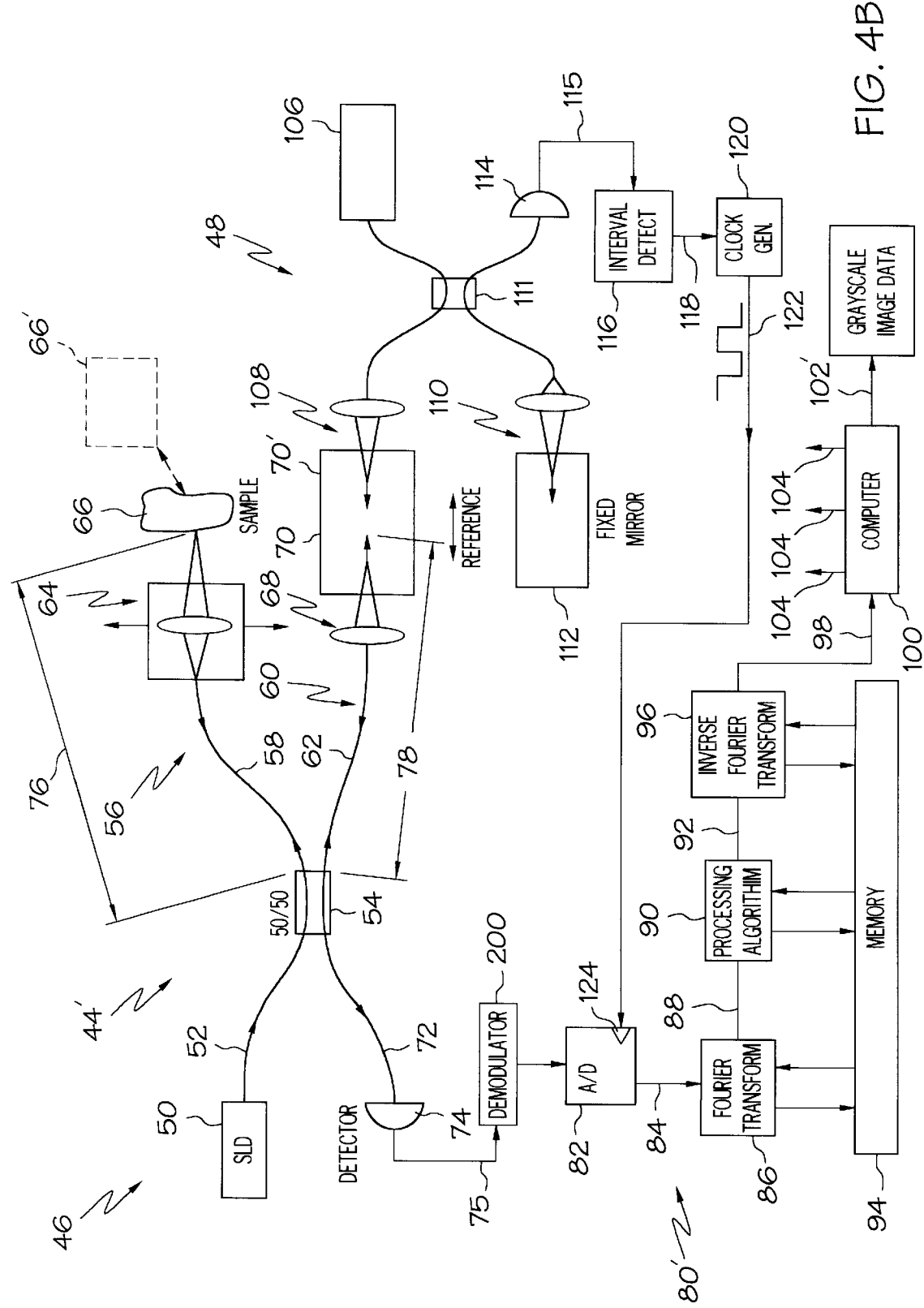
FIG. 4b is a block-diagram representation of an OCT data-acquisition system for performing the second embodiment of the OCT enhancement method of the present invention.

As shown in FIG. 4b, an OCT data acquisition system 44' for performing the demodulation technique as described above, and as illustrated in FIG. 3b, is presented. Note that identical numerals pertain to like elements. In this system, the auto-correlations and cross-correlations are passed through a demodulator 200 to acquire the magnitudes of complex envelopes of the correlation functions. Model SR830 DSP Lock-in amplifier commercially available from Stanford Research Systems, Stanford Calif., is an example of such a demodulator. If the correlation functions are digitized before demodulating, they can be demodulated using a digital demodulation algorithm implemented in software.

The magnitude of the analog cross-correlation of complex envelopes of electric fields signal acquired for each A-scan, is sent through the deconvolution scheme 80', designed to perform the steps as described above in FIG. 3b. The deconvolution scheme includes an analog-to-digital converter 82 for converting the analog cross-correlation data produced by the demodulator into a digital cross-correlation signal. The digital magnitude only cross-correlation signal is sent to a Fourier transform algorithm 86 for obtaining the cross-power spectrum estimate $S_{is}{}^m(k)$. The cross-power spectrum estimate data 88 is then sent to a processing algorithm 90 for calculating the transfer function estimate $\hat{H}^m(k)$ data 92. The processing algorithm is coupled to a memory 94 for storing the auto-power spectrum estimate data.

To obtain the auto-power spectrum estimate data, at some point in the process, the sample 66 is replaced by a sample mirror 66' and the data provided by the demodulator is the magnitude of the optical path length dependent auto-correlation function $R_{ii}(\Delta l)$ of the complex envelopes of the electric fields retroreflected from the reference mirror 70 and the sample mirror 66'. The analog-to-digital converter 82 converts the analog auto-correlation function $|R_{ii}(\Delta l)|$ into a digital signal and the Fourier transform algorithm then obtains the auto-power spectrum estimate $S_{ii}{}^m(k)$ data. When the processing algorithm 90 receives the auto-power spectrum estimate $S_{ii}{}^m(k)$ data, it stores the data in the memory 94. Accordingly, the processing algorithm will have access to the auto-power spectrum estimate $S_{ii}{}^m(k)$ for calculating the transfer function estimate $\hat{H}^m(k)$ as described above.

The transfer function estimate $H^m(k)$ of the system can be obtained according to a complex conjugate of the ratio of the cross-power spectrum estimate $S_{is}{}^m(k)$ versus the auto-power spectrum estimate $S_{ii}{}^m(k)$. Since the source spectrum has a finite bandwidth, in order to minimize noise in the impulse response, the estimate of the transfer function is multiplied by a windowing function, such as a Hanning window, to minimize noise and ringing or sidelobes in the impulse response.

We denote the transfer function estimated in this manner by $\hat{H}^m(k)$. Once the transfer function estimate $\hat{H}^m(k)$ 92 is obtained, it is transmitted to an inverse-Fourier transform algorithm 96 for obtaining the impulse response estimate $\hat{h}^m(z)$. The impulse response estimate $\hat{h}^m(z)$ data 98 is then transmitted to the computer 100 for creation of the deconvolved gray-scale or false-color image data as described above (Note that the impulse response estimate $\hat{h}^m(z)$ obtained in this manner would be similar in nature to the complex envelope of the impulse response estimate $\tilde{h}'(z)$ obtained from the correlation functions of electric fields themselves).

V. Demodulated Complex Deconvolution

As discussed above, the auto-power and cross-power spectra, $S_{ii}(k)$ and $S_{is}(k)$, are the Fourier transforms of the cross-correlation and auto-correlation functions, $R_{ii}(\Delta l)$ and $R_{is}(\Delta l)$, respectively; and the complex conjugate of the estimate of the transfer function H*(k) is the ratio of the cross-power spectra and the auto-power spectra. By utilizing both the magnitude and phase data of the demodulated correlation functions, the preferred embodiment of the OCT system shown in FIGS. 3c and 4c is able to distinguish between closely spaced reflecting sites within the sample.

Figure 3C:
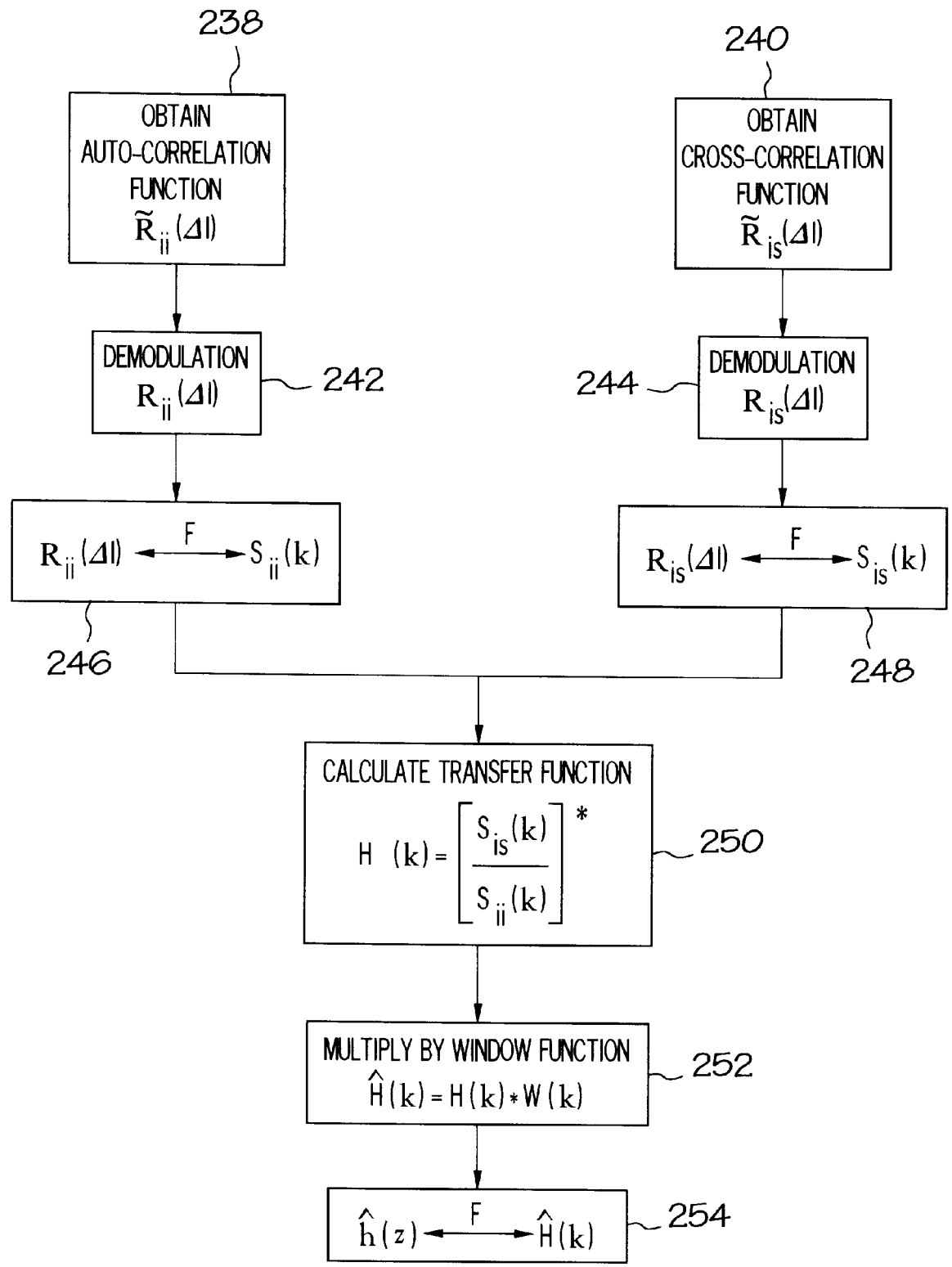
FIG. 3c is a flow-diagram representation of third embodiment of an OCT image enhancement method of the present invention.

As illustrated in FIG. 3c, the impulse response is estimated from the cross-correlation function according to the following steps: As indicated in step 238, the auto-correlation function $\tilde{R}_{ii}(\Delta l)$ is acquired from an OCT system having an optical reflector in the sample arm; and, as indicated in step 240, the cross-correlation function $\tilde{R}_{is}(\Delta l)$ is acquired from the OCT system having the biological tissue sample in the sample arm. In steps 242 and 244, the complex envelopes $R_{ii}(\Delta l)$ and $R_{is}(\Delta l)$ are acquired by demodulating the interferometric signals. In step 246, the auto-power spectrum $S_{ii}(k)$ is obtained by performing a Fourier transform on the complex envelopes of auto-correlation data $R_{ii}(\Delta l)$; and, in step 248, the cross-power spectrum $S_{is}(k)$ is obtained by performing a Fourier transform on the complex envelope of the cross-correlation function $R_{is}(\Delta l)$. As indicated in step 250, the estimate of the transfer function H(k) of the system is taken according to a complex conjugate of the ratio of the cross-power spectrum $S_{is}(k)$ versus the auto-power spectrum $S_{ii}(k)$. Since the source spectrum has a finite bandwidth, in order to minimize noise in the impulse response, as indicated in step 252, the estimate of the transfer function is multiplied by a windowing function to minimize noise and ringing or sidelobes in the impulse response. We denote the transfer function estimated in this manner by $\hat{H}(k)$. The windowing can also be performed by multiplying the window function $W(k)$ and the cross-power spectrum $S_{is}(k)$ and then dividing the product by the auto-power spectrum $S_{ii}(k)$. Alternatively, one can divide $W(k)$ by $S_{ii}(k)$ and then multiply the ratio by $S_{is}(k)$. Another way of achieving the same result is, dividing the auto-power spectrum $S_{ii}(k)$ by $W(k)$ and then using the result to divide the cross-power spectrum $S_{is}(k)$.

As indicated in step 254, the estimated impulse response $\hat{h}(z)$ is obtained by performing an inverse-Fourier transform on the estimated transfer function $\hat{H}(k)$. As discussed above, the estimated impulse response data $\hat{h}(z)$ can be transmitted to a computer 100 for further processing, such as generating a two-dimensional cross-sectional deconvolved gray-scale or false-color image of the sample.

Figure 4C:
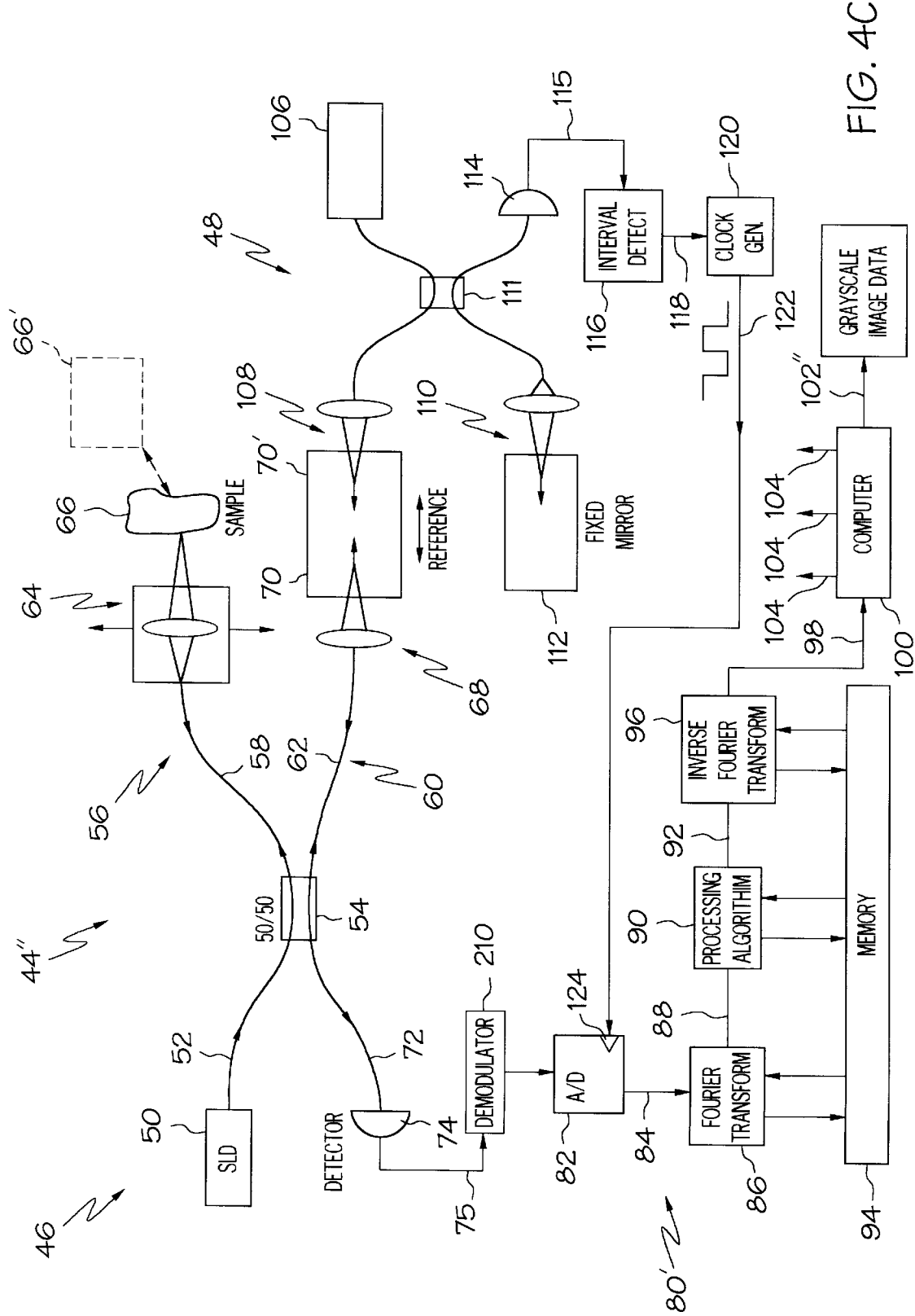
FIG. 4c is a block-diagram representation of an OCT data-acquisition system for performing the third embodiment of the OCT enhancement method of the present invention.

FIG. 4c shows an OCT data acquisition system 44" for performing the complex demodulation technique illustrated in FIG. 3c. Note that identical numerals pertain to like elements. In this system, the auto-correlation and cross-correlation interferogram data are passed through a demodulator 210 to acquire the complex envelopes of the correlation functions. Model SR830 DSP Lock-in amplifier commercially available from Stanford Research Systems, Stanford Calif., is an example of such a demodulator. If the correlation functions are digitized before demodulating, they can be demodulated using a digital demodulation algorithm implemented in software.

The analog cross-correlation of complex envelopes of electric fields acquired for each A-scan, is sent through the deconvolution scheme 80", designed to perform the steps as described above in FIG. 3c. The deconvolution scheme includes an analog-to-digital converter 82 for converting the analog cross-correlation data produced by the demodulator into a digital cross-correlation signal. The digital complex cross-correlation signal is sent to a Fourier transform algorithm 86 for obtaining the cross-power spectrum $S_{is}(k)$ data 88. The cross-power spectrum data 88 is then sent to a processing algorithm 90 for calculating the transfer function estimate $\hat{H}(k)$ data 92. The processing algorithm is coupled to a memory 94 for storing the auto-power spectrum data. To obtain the auto-power spectrum data, at some point in the process, the sample 66 is replaced by a sample mirror 66' and the data provided by the demodulator is the optical path length dependent auto-correlation function $R_{ii}(\Delta l)$ of the complex envelopes of the electric fields retroreflected from the reference mirror 70 and the sample mirror 66'. The analog-to-digital converter 82 converts the analog complex auto-correlation function into a digital signal and the Fourier transform algorithm then obtains the auto-power spectrum $S_{ii}(k)$ data. When the processing algorithm receives the auto-power spectrum $S_{ii}(k)$ data, it stores the data in the memory 94. Accordingly, the processing algorithm will have access to the auto-power spectrum $S_{ii}(k)$ for calculating the transfer function estimate $\hat{H}(k)$ as described above.

The estimate of the transfer function $H(k)$ of the system can be obtained according to a complex conjugate of the ratio of the cross-power spectrum $S_{is}(k)$ versus the auto-power spectrum $S_{ii}(k)$. Since the source spectrum has a finite bandwidth, in order to minimize noise in the impulse response, the estimate of the transfer function is multiplied by a windowing function, such as a Hanning window, to minimize noise and ringing or sidelobes in the impulse response. Generally, the windowing function is centered at dc (i.e., zero wavenumber).

We denote transfer function estimated in this manner by $\hat{H}(k)$. Once the estimate of the transfer function $\hat{H}(k)$ is calculated, the transfer function estimate $\hat{H}(k)$ data 92 is transmitted to an inverse-Fourier transform algorithm 96 for obtaining the impulse response $\hat{h}(z)$ data 98 from the transfer function estimate $\hat{H}(k)$ data. The impulse response $\hat{h}(z)$ data 98 is transmitted to a computer 100 for creation of the deconvolved gray-scale or false-color image data as discussed above. The magnitude of $\hat{h}(z)$ is used for displaying the image.

The above data acquisition system 44" provides for coherent deconvolution of the correlation data, is thus able to correct for interference occurring between light backscattered from reflecting and scattering sites in the sample that are closely spaced relative to the coherence length of the SLD.

VI. Reference Arm Optical Path-length Calibration

It is advantageous, in the above deconvolution scheme, that the auto-correlation and cross-correlation functions be measured with the sub-micron accuracy. Therefore, to enhance the accuracy of the low coherence interferogram acquisition, a long coherence length calibration interferometer 48 is incorporated into the system to accurately monitor and compensate for the inevitable velocity fluctuations of the reference mirror 70.

As shown in FIG. 4a, the calibration interferometer 48 includes a long-coherence length, narrow-band laser illumination source 106, such as a helium neon (He—Ne) laser or a distributed feed-back diode laser (DFB diode laser), a reference probe 108, and a sample probe 110. The narrow-band illumination source must have a coherence length that is longer than the region (depth) in the sample 66 that is being scanned (for example, the He—Ne laser has a coherence length of several meters).

The illumination source 106 transmits to a beam splitter 111, which separates the source signal into two illumination source signals, one being transmitted to the reference probe 108 and the other being transmitted to the sample probe 110. The reference probe 108 focuses its illumination source signal to the mirror 70' mounted on the back of the reference mirror 70 which is mounted on the galvanometer, and the sample probe 110 transmits its illumination source signal to a fixed mirror 112. The interferometer also includes a photodetector 114 for receiving the combination of light reflected back from the reference mirror 70 and the fixed mirror 112, and for producing an analog signal 115 corresponding to the intensity of light received. Because a long-coherence length illumination source 106 is used, the analog interferometric signal 115 produced by the photodetector 114 will be a relatively constant amplitude sinusoidal signal, having a frequency equal to the Doppler shift corresponding to velocity fluctuations in the reference mirror 70 experienced by the electric field in the reference arm.

The analog signal 115 produced by the photodetector 114 is sent to an interval-detect circuit 116, for detecting features in the signal 115 that are regular in time (such as zero crossings). These features 118 are fed into a clock generator circuit 120 for generating a digital clock source signal 122 for clocking (triggering) the analog-to-digital converter device 82 used in the deconvolution scheme 80. Accordingly, the sampling rate of the analog-to-digital converter 82 will be synchronized according to the fluctuations in the reference mirror 70 translation velocity detected by the calibration interferometer 48. Examples of interval-detect and clock generator circuits for use with the present invention include Tektronix 465 oscilloscope, commercially available from Tektronix, inc.

Figure 6:
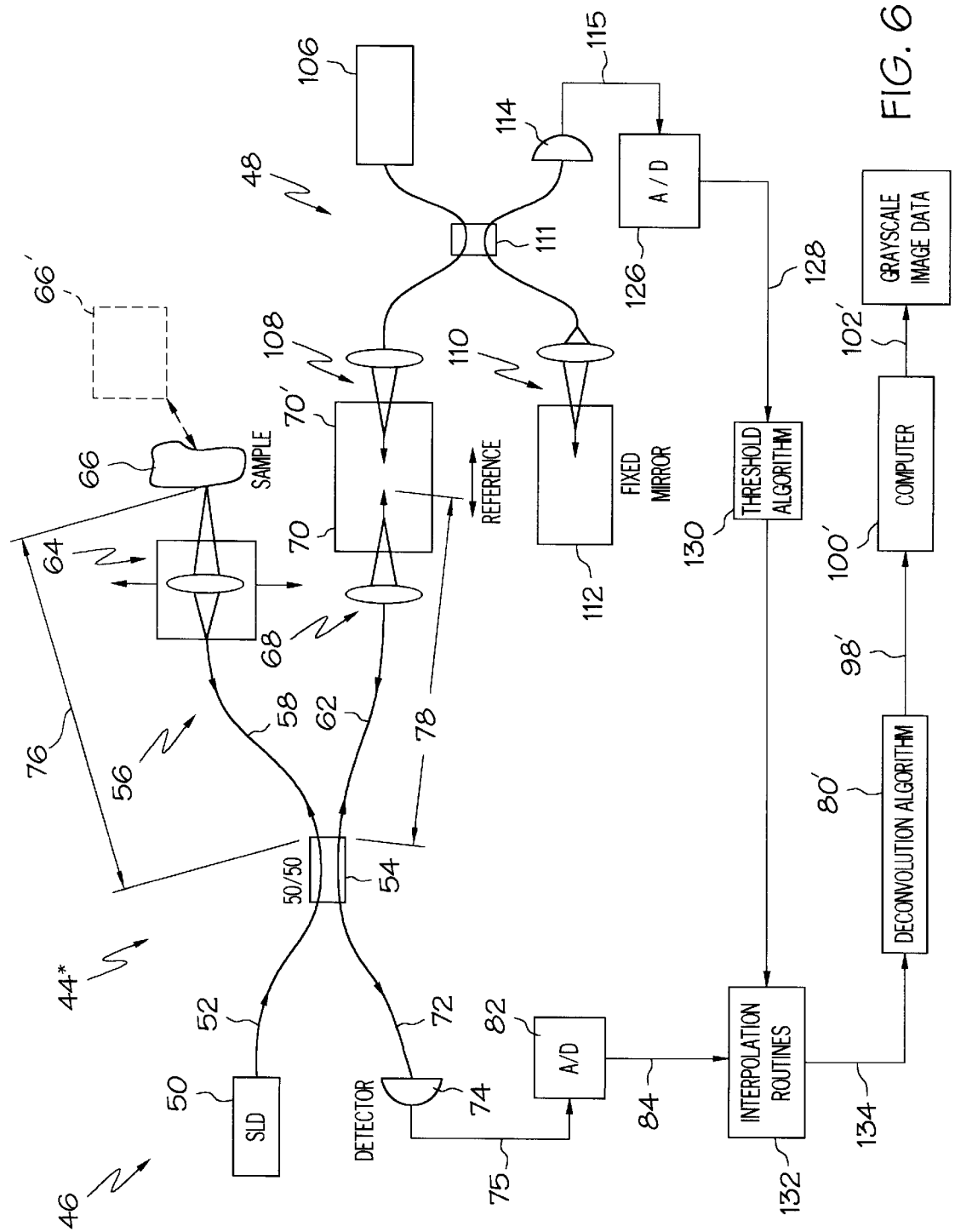
FIG. 6 is a block-diagram representation of an alternate OCT data-acquisition system for performing any of the above embodiments of the present invention.

As shown in FIG. 6, an alternate data acquisition system 44* is provided for the incorporation of the calibration interferometer 48. Note that identical numerals used in the drawings correspond to like elements. The alternate data acquisition system 44* includes an analog-to-digital converter 126 for digitizing the analog signal 115 produced by the photodetector 114. The digitized calibration signal data 128 is transmitted to a threshold-detect algorithm 130 for detecting regular features, corresponding to regular intervals of space, of the calibration interferogram (e.g., zero crossings). Both the output of the thresholding algorithm 130 and the digitized SLD interferogram data 84 are then sent to an interpolation algorithm 132 for resampling the SLD interferogram data 84 at the regular intervals developed by the thresholding algorithm 130. The resampled interferogram data 134 is then sent to optional digital demodulation and deconvolution algorithm 80' for optional demodulation and deconvolution of the resampled interferogram data 134 to generate the impulse response h(z) data 98', as described above, and that is transmitted to the computer 100' for creation of the deconvolved gray-scale or false-color image data 102'. Thresholding algorithms or interpolation algorithms were developed by the investigators.

VII. Deconvolution for Source Spectral Artifact Removal

In addition to the resolution improvement advantage of the process of deconvolution, one more advantage is the capability of using ultra high-power illumination sources, which are necessary to perform ultra high-speed OCT imaging. The problems with many high-power illumination sources is that their spectra can be substantially irregular, leading to excessive artifacts in the source spectrum. The advantage of performing coherent deconvolution, as described above, is to get rid of the irregularities of the source power spectrum and apply a customized windowing function to obtain desired shape of the source autocorrelation.

VIII. Deconvolution for Image Speckle Reduction—Experimental Results

Figure 7A:
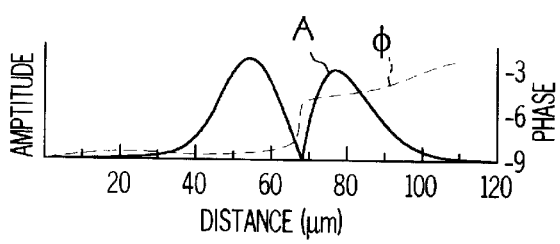
FIG. 7a is a demodulated OCT interferogram depicting two closely spaced glass-air interfaces resulting in destructive interference between them.
Figure 7B:
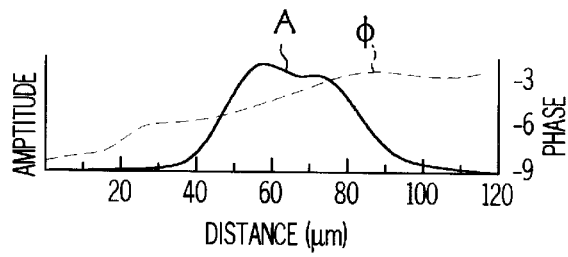
FIG. 7b is a demodulated OCT interferogram depicting two closely spaced glass-air interfaces resulting in constructive interference between them.

As shown in FIGS. 7–9, preliminary experimental data illustrates the utility of the complex deconvolution method and system described above. FIG. 7a depicts the amplitude (A) and phase ($\phi$) of a demodulated A-scan of two closely spaced reflecting sites within a sample, where the reflections interfere destructively with each other at the center since the waves reflected from the sites are 180° out of phase with each other (note the phase shift in the demodulated data in the center of the figure). FIG. 7b depicts the amplitude (A) and phase ($\phi$) of a demodulated A-scan of two closely spaced reflecting sites within a sample, where the reflections interfere constructively with each other at the center since the waves reflected from the sites are in phase with each other. Accordingly, the separation between the sites in FIG. 7a and FIG. 7b differ from each other by a quarter wavelength. The above destructive or constructive interference is the cause of "speckle" in OCT images resulting from many closely spaced reflecting sites within a sample.

Figure 8A:
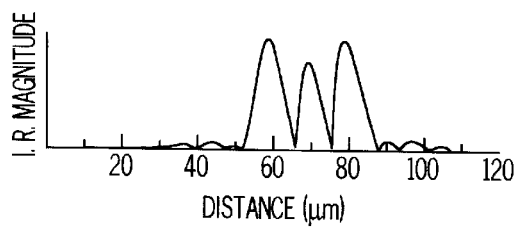
Figure 8B:
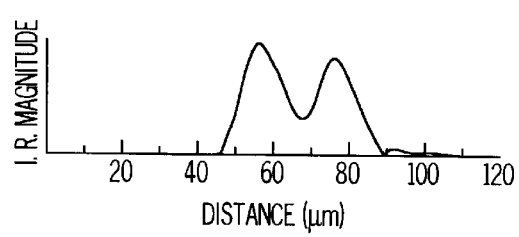
FIG. 8b shows magnitude-only deconvolution of the interferogram of FIG. 7b.
Figure 9A:
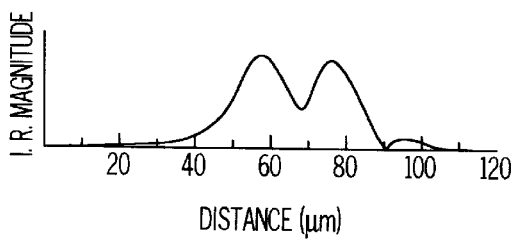
Figure 9B:
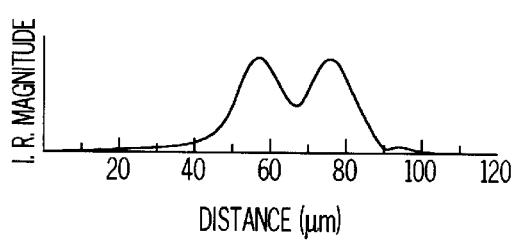
FIG. 9b shows complex deconvolution of the interferogram of FIG. 7b.

As shown in FIGS. 8a and 8b, deconvolution using magnitude-only data provides inaccurate spectral estimation leading to errors in the calculated impulse response in both cases. Note the false zero created in FIG. 8a. As shown in FIGS. 9a and 9b, complex deconvolution provides an accurate reconstruction of the original reflecting sites, notably without the false zero in FIG. 9a.

IX. Iterative Deconvolution

Embodiments of the invention described above calculate the impulse response by first obtaining cross-power spectra and auto-power spectra, then obtaining a transfer function of the system by taking the complex conjugate of the ratio of the cross-power spectra to the auto-power spectra, and then obtaining the optical impulse response of the system by performing an inverse-Fourier transform on the transfer function. The optical impulse response of the system may also be generated without having to compute the auto-power and cross-power spectra. In particular, a constrained iterative restoration algorithm may be employed to obtain an estimate of the impulse response h" achieved using prior knowledge of the properties of h. This prior knowledge can be expressed using a constraint operator C.

The demodulation electronics of most prior-art OCT systems acquire only the magnitude of the cross-correlation function, $|R_{is}(\Delta l)|$. For magnitude-only OCT images one could impose the positivity constraint as described in Schafer, R. W., Merserau, R. M., and Richards, M. A., "Constrained Iterative Restoration Algorithms," Proc. IEEE, 1981, 69, pp. 432–450. We can write an approximation of Eq. (9), above, as $|R_{is}(\Delta l)|=|R_{ii}(\Delta l)\otimes h'(-\Delta l)|$ where h' is an approximation of h and equals to |h| for isolated reflections. h' is a positive quantity. Its estimates can be obtained by the method of successive approximations described by:

$$\hat{h}_{l+1} = C\hat{h}_l + \lambda(|R_{is}| - |R_{ii}| \otimes C\hat{h}_l). \tag{11}$$

where l is an iteration counter, $\lambda$ is a parameter and $\hat{h}_l(n)$ is the lth estimate of h'. We can choose the initial guess as $\hat{h}_0=\lambda|R_{is}|$. The conditions required for the convergence of the iterative algorithm are given by:

$$0<\lambda\leq 2/\max(S'_{ii}(k)),\ Re[S'_{ii}(k)]>0. \tag{12}$$

where $S'_{ii}(k)$ is a Fourier transform of $|R_{ii}(\Delta l)|$. Our measurements indicate that for the SLD source in our OCT system $Re[S'_{ii}(k)]>0$ since $|R_{ii}(\Delta l)|$ of the SLD has an approximately Gaussian shape. Since the peak of $S'_{ii}(k)$ is at zero frequency, the maximum of $S'_{ii}(k)$ is just the area under $|R_{ii}(\Delta l)|$.

In a preliminary application of the above constrained iterative restoration algorithm, deconvolution on a magnitude-only OCT image of a fresh onion specimen was performed, leading to striking image enhancement. Sharp boundaries of cellular structure were clearly resolved. The dynamic range (defined as the ratio of the peak of $|R_{ii}(\Delta l)|$ and the standard deviation of the magnitude of noise) was decreased by only 2 dB since minimal noise is generated. Ten iterations are sufficient to achieve desired results, however thirty iterations were performed in the preliminary application.

X. Conclusion

While describing the deconvolution methods of the present invention, we talk about the scanning Michelson interferometer where the reference arm length is mechanically scanned by translating the reference mirror. It is to be understood that the deconvolution methods described herein are applicable to any interferometric device which estimates the correlation functions described above. The deconvolution algorithms are also applicable to any device which measures the auto-power spectra and cross-power spectra. Thus, the methods of the present invention are applicable to any device capable of measuring any of the above mentioned quantities whether the device operates in free space or is fiber optically integrated. Also, the methods of the present invention are equally applicable in situations where a measuring device is coupled to an endoscope or a catheter or any other diagnostic instrument.

The impulse response was described above as a function of depth z or time or pathlength difference $\Delta l$. It is to be understood that the impulse response can also be estimated using our deconvolution methods as a function of the difference between the optical time delay from the radiation source to the reference reflector (i.e., reference path) and the optical time delay from the radiation source to the sample (i.e., sample path); the difference is denoted by $\tau = \Delta l/v$.

Although a low temporal coherence source is useful in making the measurements in OCDR and OCT, it is to be understood that a high temporal coherence source can be used with our deconvolution methods of the present invention to improve axial resolution.

Whenever we use a mirror to reflect light and perform measurements such as auto-correlation and cross-correlation functions, one can achieve the similar results by using any other optical reflector. Also we describe that the auto-correlation function is measured using a strong reflector which replaces the specimen in the sample arm. It should be noted that the auto-correlation can also be measured using a strong reflector which is a part of the specimen itself. The auto-correlation function can also be modeled using the information about the radiation source. It can be also calculated using the knowledge of the source power spectral density. For instance, the inverse Fourier transform of the measured source power spectrum would provide an estimate of the auto-correlation function.

The windowing of the transfer function estimate is similar to filtering the estimate of the transfer function using a filter function such as Wiener filter. These filters are used to eliminate ringing in the image as well as for noise reduction, and thus they have a similar function as the windowing functions. These filters and windows can be applied in frequency domain as well as in space/time domain. In space/time domain the window or filter kernels convolve with the cross-correlation data in order to achieve the results equivalent to those obtained by multiplication in frequency domain.

Having described the invention in detail and by reference to the drawings, it will be apparent that modification and variations are possible without departing from the scope of the invention as defined in the following claims.

What is claimed is:

1. A method for generating interferogram data of a sample in an optical coherence tomography system, the optical coherence tomography system including a main interferometer having an optical radiation source and a sample arm, the method comprising the steps of:

acquiring auto-correlation data for the main interferometer;

acquiring cross-correlation data from the main interferometer with the sample in the sample arm; and processing the auto-correlation data and the cross-correlation data to produce an optical impulse response of the tissue.

2. The method of claim 1, wherein the processing step includes the step of performing complex deconvolution on the auto-correlation data and the cross-correlation data.

3. The method of claim 2, wherein the processing step includes the step of performing coherent demodulation on the auto-correlation data and the cross-correlation data.

4. The method of claim 3, wherein the processing step includes the steps of:

obtaining an auto-power spectrum from the auto-correlation data by performing a Fourier transform on a magnitude portion of the demodulated auto-correlation data;

obtaining a cross-power spectrum from the cross-correlation data by performing a Fourier transform on a magnitude portion of the demodulated cross-correlation data;

obtaining a transfer function from the cross-power spectrum and auto-power spectrum by obtaining a complex conjugate of a ratio of the cross-power spectrum to the auto-power spectrum; and obtaining the optical impulse response by performing an inverse Fourier transform on the transfer function.

5. The method of claim 3, wherein the processing step includes the steps of:

obtaining an auto-power spectrum from the auto-correlation data by performing a Fourier transform on magnitude and phase portions of the demodulated auto-correlation data;

obtaining a cross-power spectrum from the cross-correlation data by performing a Fourier transform on magnitude and phase portions of the demodulated cross-correlation data;

obtaining a transfer function from the cross-power spectrum and auto-power spectrum by obtaining a complex conjugate of a ratio of the cross-power spectrum to the auto-power spectrum; and obtaining the optical impulse response by performing an inverse Fourier transform on the transfer function.

6. The method of claim 1, wherein the processing step includes the steps of:

obtaining an auto-power spectrum from the auto-correlation data by performing a Fourier transform on the auto-correlation data;

obtaining a cross-power spectrum from the cross-correlation data by performing a Fourier transform on the cross-correlation data;

obtaining a transfer function from a ratio of the cross-power spectrum to the auto-power spectrum; and obtaining the optical impulse response by performing an inverse Fourier transform on the transfer function.

7. The method of claim 6, wherein the processing step further includes the step of performing coherent demodulation on the auto-correlation data and the cross-correlation data.

8. The method of claim 6, further comprising the step of obtaining a windowed transfer function.

9. The method of claim 8, wherein the windowing function is customized according to the optical radiation source.

10. The method of claim 6, further comprising the steps of:

generating a calibration interferogram with a calibration interferometer having a high-coherence radiation source, a sample arm, an optical reflector in the sample arm, a reference arm, and a scanning optical reflector in the reference arm, the scanning optical reflector being coupled to a scanning device of the main interferometer;

detecting regular features in the calibration interferogram;

generating a digital clock signal from the regular features detected from the calibration interferogram; and synchronizing the cross-correlation data and auto-correlation data acquisition steps using the digital clock signal.

11. The method of claim 6, further comprising the step of obtaining a filtered transfer function.

12. The method of claim 1, wherein the processing step includes the steps of:
    obtaining an auto-power spectrum from the auto-correlation data by performing a Fourier transform on the auto-correlation data;
    obtaining a cross-power spectrum from the cross-correlation data by performing a Fourier transform on the cross-correlation data;
    obtaining a transfer function from the cross-power spectrum and auto-power spectrum by taking a ratio of the cross-power spectrum to the auto-power spectrum; and
    obtaining the optical impulse response by performing an inverse Fourier transform on the transfer function.

13. The method of claim 1, further comprising the step of monitoring reference arm path length of the main interferometer, wherein the processing step includes the step of compensating for velocity fluctuations detected during the monitoring step.

14. The method of claim 1, further comprising the steps of:
    generating a calibration interferogram with a calibration interferometer having a high-coherence radiation source, a sample arm, an optical reflector in the sample arm, a reference arm, and a scanning optical reflector in the reference arm, the scanning optical reflector being coupled to a scanning device of the main interferometer;
    detecting regular features in the calibration interferogram;
    generating a digital clock signal from the regular features detected from the calibration interferogram; and
    synchronizing the cross-correlation data and auto-correlation data acquisition steps using the digital clock signal.

15. The method of claim 1, further comprising the steps of:
    generating a calibration interferogram with a calibration interferometer having a high-coherence radiation source, a sample arm, an optical reflector in the sample arm, a reference arm, and a scanning optical reflector in the reference arm, the scanning optical reflector being coupled to a scanning device of the main interferometer;
    detecting regular intervals in the calibration interferogram;
    digitizing the auto-correlation interferogram data and the cross-correlation interferogram data; and
    resampling the digitized auto-correlation interferogram data and the digitized cross-correlation interferogram data at the regular intervals.

16. The method of claim 1, wherein the step of acquiring auto-correlation data includes the step of placing an optical reflector in the sample arm of the main interferometer.

17. The method of claim 1, further comprising the step of detecting an envelope of the impulse response.

18. The method of claim 17 wherein the detecting step includes the step of demodulating the impulse response.

19. The method of claim 1, further comprising the step of detecting a magnitude portion of the impulse response.

20. The method of claim 1, wherein the processing step includes the step of performing iterative deconvolution on the auto-correlation and cross-correlation data.

21. The method of claim 1, further comprising the step of incorporating a sample probe portion of the main interferometer into an endoscopic or surgical instrument.

22. The method of claim 21, further comprising the step of scanning the endoscopic or surgical instrument along a portion of a patient's gastrointestinal tract tissue to monitor fine structures.

23. An optical coherence tomography system comprising:
    a low coherence optical radiation source;
    a first translating reference optical reflector;
    a first beam splitter, splitting the radiation source into two paths, one path directed to a sample and the other path directed to the first reference reflector;
    a first beam combiner for combining beams reflected from the sample with beams reflected from the first reference reflector;
    a first optical detector for acquiring a data package from the first beam combiner;
    a Fourier transform device, operatively coupled to an output of the first optical detector for generating a power spectrum from the data package;
    a processor device, operatively coupled to an output of the Fourier transform device and having access to a memory device, for generating a transfer function with the power spectrum; and
    an inverse-Fourier transform device, operatively coupled to an output of the processor device, for generating an impulse response from the transfer function.

24. The optical coherence tomography system of claim 23, further comprising:
    a demodulator device, operatively coupled between the first optical detector and the Fourier transform device.

25. The optical coherence tomography system of claim 24, further comprising:
    an analog-to-digital converter device, operatively coupled between the demodulator device and the Fourier transform device.

26. The optical coherence tomography system of claim 25, further comprising:
    a calibration interferometer, including a high-coherence source, a sample arm, a reference arm, a calibrating optical reflector in the sample arm, and a second translating reference reflector in the reference arm, a second beam splitter, splitting the high-coherence source into two paths, one path directed to the calibrating optical reflector in the sample arm and the other path directed to the second reference reflector in the reference arm coupled to the first translating reference optical reflector, a second beam combiner combining beams reflected from the calibration optical reflector in the sample arm with beams reflected from the second reference reflector in the reference arm, and a second optical detector acquiring a calibration interferogram from the second beam combiner; and
    an interval detection device coupled to an output of the second optical detector, detecting regular features in the calibration interferogram; and
    a clock generator, operatively coupled to an output of the interval detection device and generating a digital clock signal from the regular features detected in the calibration interferogram by the interval detection device;
    wherein, the analog-to-digital converter device includes a clock input operatively coupled to an output of the clock generator, whereby the analog-to-digital converter is synchronized by the calibration interferometer.

27. The optical coherence tomography system of claim 23, further comprising:
an analog-to-digital converter device, operatively coupled between the first optical detector and the Fourier transform device.

28. The optical coherence tomography system of claim 23, further comprising:
a calibration interferometer, including a high-coherence source, a sample arm, a reference arm, a calibration optical reflector in the sample arm, and a second translating reference reflector in the reference arm, a second beam splitter, splitting the high-coherence source into two paths, one path directed to the calibration optical reflector in the sample arm and the other path directed to the second reference reflector in the reference arm coupled to the first translating reference optical reflector, a second beam combiner combining beams reflected from the calibration optical reflector in the sample arm with beams reflected from the second reference reflector in the reference arm, and a second optical detector acquiring a calibration interferogram from the second beam combiner; and
a thresholding device operatively coupled to an output of the second optical detector, detecting regular features in the calibration interferogram; and
an interpolation device, operatively coupled to an output of the interval detection device and operatively coupled between the first optical detector and the Fourier transform device, the interpolation device resampling the interferogram data from the first optical detector at regular intervals developed by the thresholding device.

29. An optical coherence tomography system comprising:
a main interferometer including an optical radiation source and a sample arm, the main interferometer generating a cross-correlation data output of a sample in the sample arm;
a means for generating or calculating an auto-correlation data output; and
a data processing system, operatively coupled to an output of the main interferometer, processing the auto-correlation data and the cross-correlation data to produce an optical impulse response of the sample.

30. The optical coherence tomography system of claim 29, wherein the data processing system includes:
a Fourier transform device, operatively coupled to the output of the main interferometer, generating an auto-power spectrum from the auto-correlation data and generating a cross-power spectrum from the cross-correlation data;
a processor device, operatively coupled to an output of the Fourier transform device, generating a transfer function using the auto-power spectrum and the cross-power spectrum; and
an inverse-Fourier transform device, operatively coupled to an output of the processor device, generating an impulse response from the transfer function.

31. The optical coherence tomography system of claim 30, further comprising a means for generating a multi-dimensional image from multiple outputs of the inverse-Fourier transform device.

32. The optical coherence tomography system of claim 29, further comprising:
a scanner for scanning a reference optical reflector or a sample probe of the main interferometer;
a calibration interferometer, including a high-coherence source, a sample arm, a calibration optical reflector in the sample arm, and a reference optical reflector coupled to the scanner of the main interferometer, the calibration interferometer generating a calibration interferogram;
an interval detection device coupled to an output of the calibration interferometer, detecting regular features in the calibration interferogram; and
a clock generator, operatively coupled to an output of the interval detection device, generating a digital clock signal from the regular features detected in the calibration interferogram by the interval detection device;
wherein, the data processing system includes a clock input operatively coupled to an output of the clock generator, whereby the data processing system is synchronized by the calibration interferometer.

33. The optical coherence tomography system of claim 29, further comprising:
a scanner for scanning a reference optical reflector or a sample probe of the main interferometer;
a calibration interferometer, including a high-coherence source, a sample arm, a calibration optical reflector in the sample arm, and a reference optical reflector coupled to the scanner of the main interferometer, the calibration interferometer generating a calibration interferogram;
a thresholding device operatively coupled to an output of the calibration interferometer, detecting regular features in the calibration interferogram; and
an interpolation device, operatively coupled to an output of the interval detection device and operatively coupled between the main interferometer and the data processing system, the interpolation device resampling the auto-correlation and cross-correlation interferogram data from the main interferometer at regular intervals developed by the thresholding device.

34. The optical coherence tomography system of claim 29, further comprising a demodulator device operatively coupled between the main interferometer and the data processing system.

35. The optical coherence tomography system of claim 29, wherein the main interferometer includes a sample probe incorporated into an endoscopic or surgical examination device.

36. An optical coherence tomography system, comprising:
an electromagnetic radiation source generating source radiation;
a reference optical reflector;
means for directing the source radiation to a sample;
means for directing the source radiation to a reference reflector;
means for combining reflected radiation from the sample and from the reference reflector, to produce combined reflected radiation; and
means for obtaining an estimate of an optical impulse response from the combined reflected radiation.

37. The optical coherence tomography system of claim 36, further comprising:
means for adjusting the optical path length between the radiation source and the reference reflector; and
means to produce a one-dimensional data set from the estimated impulse response.

38. The optical coherence tomography system of claim 37, further comprising means for correcting irregularities in a scan rate of the optical path length adjustment means.

39. A method for generating interferogram data of a sample in an optical coherence tomography system, the optical coherence tomography system including a main interferometer having an optical radiation source and a sample arm, the method comprising the steps of:

acquiring auto power spectra for the main interferometer;

acquiring cross power spectra from the main interferometer with the sample in the sample arm; and processing the auto power spectra and the cross power spectra to produce an optical impulse response of the tissue.

\* \* \* \* \*